(12) United States Patent
Bohner et al.

(10) Patent No.: US 12,188,003 B1
(45) Date of Patent: Jan. 7, 2025

(54) METHODS AND SYSTEMS FOR PERFORMING BIOCHEMICAL PROCESSES

(71) Applicant: Trisk Bio Ltd., Stevenage (GB)

(72) Inventors: Gergo Bohner, Cambridge (GB); Adam Luke Hiles, Leighton Buzzard (GB); Samuel Isidor Jones, London (GB); Kevin Lynagh, Tacoma, WA (US); Ryan Olf, Cambridge (GB); Gabor Pap, Stevenage (GB); Spencer Ryan Wilson, London (GB); Thomas Felix Martin Cummings, London (GB)

(73) Assignee: Trisk Bio Ltd., Stevenage (GB)

( * ) Notice: Subject to any disclaimer, the term of this patent is extended or adjusted under 35 U.S.C. 154(b) by 58 days.

(21) Appl. No.: 18/374,098

(22) Filed: Sep. 28, 2023

(51) Int. Cl.
*C12M 1/00* (2006.01)
*C12M 1/34* (2006.01)

(52) U.S. Cl.
CPC ............ *C12M 47/12* (2013.01); *C12M 23/40* (2013.01); *C12M 29/04* (2013.01); *C12M 41/00* (2013.01)

(58) Field of Classification Search
CPC ...... C12M 47/12; C12M 23/40; C12M 29/04; C12M 41/00
USPC ........................................................ 435/286.5
See application file for complete search history.

(56) References Cited

U.S. PATENT DOCUMENTS

| | | |
|---|---|---|
| 3,000,655 A | 9/1961 | Piet et al. |
| 3,674,290 A | 7/1972 | McNally |
| 4,030,494 A | 6/1977 | Tenczar |
| 4,349,508 A | 9/1982 | Liede |
| 4,453,566 A | 6/1984 | Henderson, Jr. et al. |
| 4,497,773 A | 2/1985 | Kuelzow et al. |
| 4,694,859 A | 9/1987 | Smith, III |
| 5,082,245 A | 1/1992 | Kast |
| 5,316,347 A | 5/1994 | Arosio |
| 5,649,563 A | 7/1997 | Shimano |
| 5,927,318 A | 7/1999 | Ishibashi et al. |
| 6,513,837 B2 | 2/2003 | Fujikawa et al. |
| 9,675,520 B2 | 6/2017 | Rogers et al. |

(Continued)

FOREIGN PATENT DOCUMENTS

| | | |
|---|---|---|
| CA | 2292087 | 6/2000 |
| CN | 109578705 | 4/2019 |

(Continued)

*Primary Examiner* — Michael L Hobbs
*Assistant Examiner* — Lenora A Abel
(74) *Attorney, Agent, or Firm* — Weiss & Arons LLP

(57) ABSTRACT

Provided herein is a method for processing a liquid sample, utilizing a first component including an interface side and at least 3 sample containers or tanks; and a second component including a connector manifold. The method may include the step of reversibly connecting a reagent container, a filtration apparatus, and a chromatography apparatus to the manifold; reversibly connecting the first component to the connector manifold; pressurizing the first sample tank; transferring the sample into the filtration apparatus; passing the sample through a filter; transferring the sample into the second sample tank; transferring the sample into the chromatography apparatus; transferring the reagent into the chromatography apparatus; and transferring the sample to the third sample tank. Some or all transfers may be routed via the connector manifold and the interface side.

5 Claims, 29 Drawing Sheets

(56) References Cited

U.S. PATENT DOCUMENTS

| | | | |
|---|---|---|---|
| 10,060,565 | B2 | 8/2018 | Bishop, Jr. |
| 2003/0040104 | A1 | 2/2003 | Barbera-Guillem |
| 2012/0089930 | A1 | 4/2012 | Stanton, IV et al. |
| 2015/0061282 | A1 | 3/2015 | Faldt et al. |
| 2016/0040112 | A1* | 2/2016 | Coppeta ................ C12M 27/18 435/293.1 |
| 2018/0371399 | A1 | 12/2018 | Griffin et al. |
| 2019/0192844 | A1 | 6/2019 | Wegener et al. |
| 2021/0002602 | A1 | 1/2021 | Ludlam et al. |
| 2021/0102156 | A1 | 4/2021 | Griffin et al. |
| 2022/0299144 | A1 | 9/2022 | Bonnyman et al. |
| 2022/0326248 | A1 | 10/2022 | Miltenyi et al. |
| 2023/0285734 | A1 | 9/2023 | Madsen et al. |

FOREIGN PATENT DOCUMENTS

| | | |
|---|---|---|
| EP | 0230864 | 8/1987 |
| WO | WO2022/256403 | 12/2022 |

* cited by examiner

METHODS AND SYSTEMS FOR PERFORMING BIOCHEMICAL PROCESSES

FIELD OF TECHNOLOGY

Aspects of the disclosure relate to methods and systems for conducting biochemical purification processes, for example purification of viral capsids and products derived from cells.

BACKGROUND

Biochemical purification protocols often involve multiple filtration and chromatography steps, each with its own dedicated apparatus. Individual components must be manually cleaned, assembled, and leak tested at each stage, significantly contributing to labor costs, run time and complexity, and downtime between runs. Furthermore, the significant reliance on manual assembly and disassembly of connections introduces potential for human error in adherence to the specified parameters, proper sterile technique, and audit trail documentation. Methods with improved efficiency, reliability, and reproducibility are urgently needed.

SUMMARY OF THE DISCLOSURE

It is an object of the present disclosure to provide a more adaptable system architecture for biochemical purification processes, for example isolation of products derived from cells. It would be advantageous to enable modifications of such processes without labor-intensive modification of tubing connections.

It is a further object of the present disclosure to decrease downtime between biochemical purification runs.

It is a further object of the present disclosure to provide an apparatus for biochemical purification processes that enables process modification by simple replacement of portable modules or components thereof.

It is a further object of the present disclosure to provide a system for biochemical purification processes that enables fully or largely automated process execution.

It is a further object of the present disclosure to reduce the footprint of biochemical purification processes and reduce the amount of equipment required for such processes.

It is a further object of the present disclosure to provide an integrated solution for upstream and downstream steps for biotechnological processes, such as incubation of virus-producing cells, lysis, and downstream virus purification steps.

The present disclosure improves upon conventional approaches by providing a system of interconnected tanks and rigid and flexible tubing for gas, steam, and liquid, some aspects of which can be maintained as a closed system accessed only via controlled interfaces. The controlled interfaces enable the system to maintain a sealed boundary between the internal flow paths and the external environment, preventing corruption of sensitive biochemical samples material. The interfaces may be amenable to robotic attachment and detachment.

The system may include sample containers, also referred to herein as "tank(s)", to facilitate various stages of a biochemical purification process. Additions to and samples to, from, and between the tanks may be performed using compressed air to actuate fluid movement. The air may pressurize the internal space of a liquid-containing tank and induce liquid flow out of the tank into a destination container (e.g., a filtration or chromatography apparatus or another sample container). These processes may be automated.

The air may be sterilized. Air used for transferring liquids in this way can be sterilized by passage through sterile filters, in some cases prior to reaching the sample tank. These filters themselves may be steam sterilized and tested for filter integrity via automated processes.

Provided herein is a system, in accordance with principles of the disclosure. The system may be suitable for processing a liquid sample. The system may be suitable for performing a biochemical purification protocol. The protocol may be a virus capsid purification protocol. The protocol may be another biochemical fractionation protocol.

The system may include a first component and a second component. The second component may be reversibly connected to the first component. The first and second components may also be referred to as the first and second compartments, respectively.

As used herein, the term reversibly may refer to a connection that can be dismantled, while preserving the structure of the mentioned lines and their ability to be cleaned and reused in a closed system. In some embodiments, the connection is configured to exclude external contaminants. In some embodiments, the connection is a sterile connection.

The first component may include an interface side. The interface side may include at least 4 orifices. The interface said may include a first orifice, a second orifice, a third orifice, and a fourth orifice.

The first component may include a pressure actuator.

The first component may include at least 2 sample containers. The first component may include a first sample container and a second sample container.

As used herein, a sample container may refer to a container that is configured to contain a liquid biological product or sample.

The first component may include a gas conduit. The gas conduit may connect the first sample container to the pressure actuator.

The first component may include at least 2 sample conduits. The first component may include a first sample conduit and a second sample conduit.

The first component may include at least 4 connectors. The first component may include a first connector, a second connector, a third connector, and a fourth connector. These connectors may be referred to herein as interface-side connectors.

The first component may include a reagent conduit.

In some embodiments, the first sample conduit may be connected to the first sample container and the first connector. In some embodiments, the second sample conduit may be connected to the second sample container and the second connector. In some embodiments, the reagent conduit may be connected to the third and fourth connectors. In some embodiments, the first, second, third, and fourth connectors may be disposed in the first, second, third, and fourth orifices, respectively.

The described second component may include a connector manifold. The connector manifold may include at least 4 connectors. The connector manifold may include a fifth connector, a sixth connector, a seventh connector, and an eighth connector. These connectors may be referred to herein as manifold-side connectors.

In some embodiments, reference herein to connectors located in, or disposed in an interface or connector manifold may indicate that the connectors are embedded in the interface or manifold.

The second component may include a fractionation moiety. The fractionation moiety may be reversibly connected to the fifth sixth, and seventh connectors.

As used herein, the term fractionation moiety refers to an apparatus configured to perform a biochemical fractionation or separation procedure. The fractionation moiety may be a filtration apparatus. The moiety may be a frontal-flow filtration apparatus. The moiety may be a tangential-flow filtration apparatus. The moiety may be a chromatography apparatus. Both filtration and chromatography moieties may be present in the system. Frontal-flow filtration, tangential-flow filtration, and chromatography moieties may all be present in the system.

The second component may include a reagent container. The reagent container may be reversibly connected to the eighth connector. As used herein, the term reagent container refers to a container configured to contain a liquid reagent.

In some embodiments, the first connector may be connected to the fifth connector. In some embodiments, the second connector may be connected to the sixth connector. In some embodiments, the third connector may be connected to the seventh connector. In some embodiments, the fourth connector may be connected to the eighth connector.

Reference herein to fluid lines and pressure lines in either compartment is not intended to convey that certain lines are designated exclusively for either fluid or pressure. Individual lines connecting the central and peripheral compartments may be dual-use lines. Whether a line is used for liquid or pressurized gas may depend on the configuration of the particular upstream process. In other embodiments, each line may be used for a liquid, a pressurized gas, or both successively a liquid and a pressurized gas (in either order), during a particular bioreactor run. In some embodiments, a pressurized gas may be used to flush out a line after passage of liquid through the line, for example in order to achieve a high transfer yield.

In embodiments of the described methods and systems, the connectors joining the 2 sides of an interface between different compartments may be hydraulic connectors. In some embodiments, the connectors may be pneumatic couplings. The couplings may include two parts. The two parts may be the quick coupling, or the female part, and the plug-in, nipple, or male part.

The connectors may be configured to automatically shut off liquid flow when disconnected. The connectors may be spring loaded or use other technologies known in the art, for example ball bearings, to enable automatic shutoff. The connectors may be quick couplings. They may include a floating ball valve that closes automatically when the coupling ends are disconnected from one another. In some embodiments, the connections may be able to withstand at least 10 bar pressure.

In some embodiments, the connectors may be flat-face connectors. Connecting the ends may engage the movement of internal springs. Disconnecting the ends may automatically close the lumen. This mechanism may act as an automatic valve.

In some embodiments, the connectors may be no-spill, no-drip, or dry break connectors. In some embodiments, the connectors are configured to impede air ingress into the flow path during connection and disconnection. Alternatively, or in addition, the connectors are configured to impede liquid egress from the flow path during connection and disconnection.

In some embodiments, the connectors are internally valved. In other embodiments, the connectors are externally valved.

DETAILED DESCRIPTION

Figure 1:
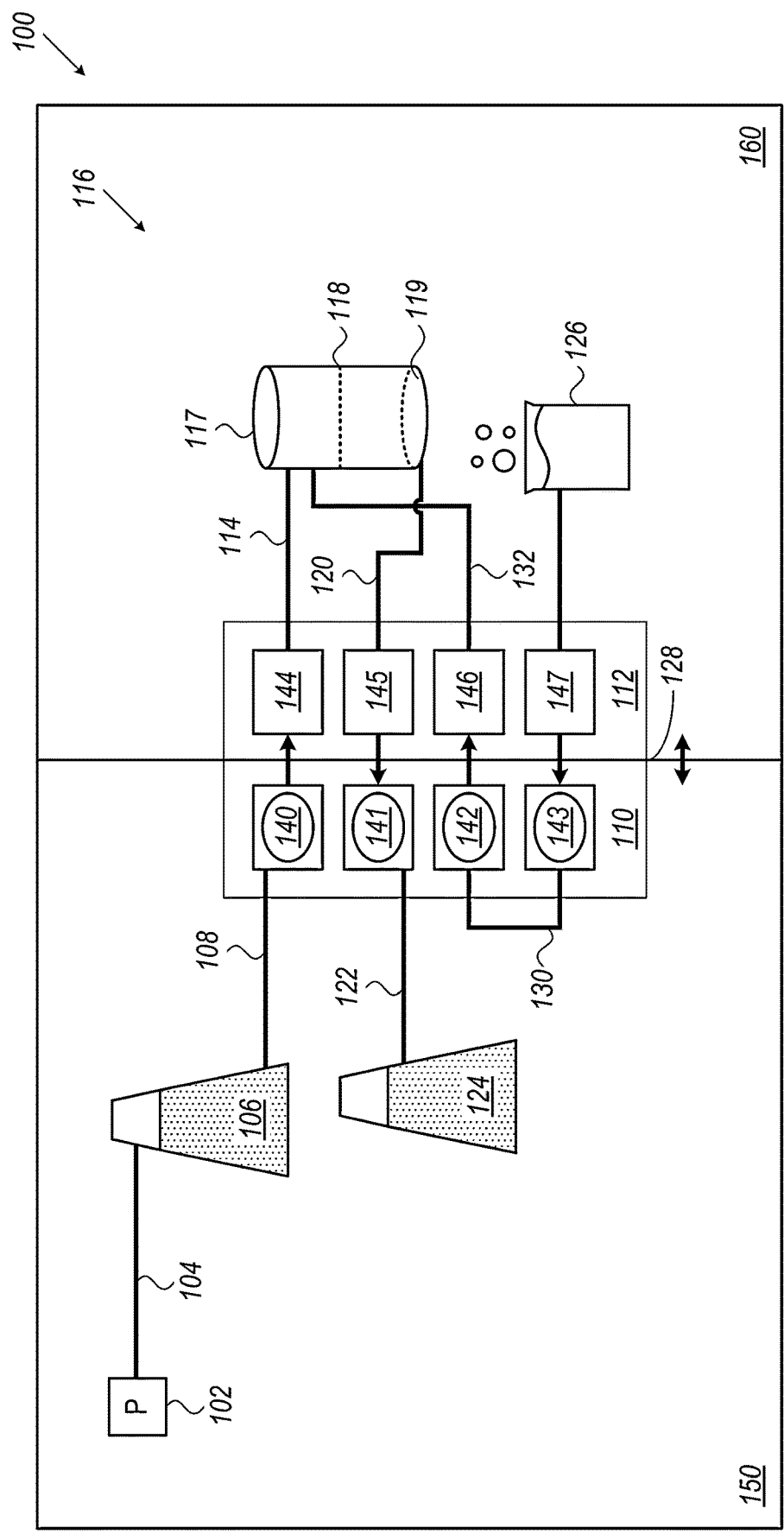
FIG. 1 depicts a schema of a system for biochemical purification.

Provided herein is a system, in accordance with principles of the disclosure. The system may be suitable for processing a liquid sample. The system may be suitable for performing a biochemical purification protocol. The protocol may be a virus capsid purification protocol. The protocol may be another biochemical fractionation protocol.

The system may include a first compartment and a second compartment. The second compartment may be reversibly connected to the first compartment. The second compartment may be reversibly connectable to the first compartment.

The first compartment may include an interface side. The interface side may include at least 4 orifices. The interface side may include a first orifice, a second orifice, a third orifice, and a fourth orifice. The interface side may include at least a first orifice, a second orifice, a third orifice, and a fourth orifice.

The first compartment may include a pressure actuator. The pressure actuator may be the first pressure actuator among a plurality of pressure actuators. The pressure actuator may be the only pressure actuator in the system. The term "first pressure actuator" is not intended to require the presence of additional pressure actuators in the system.

The first compartment may include at least 2 sample containers. The first compartment may include a first sample container and a second sample container.

The first compartment may include a gas conduit. The conduit may be the first gas conduit among a plurality of gas conduits. The conduit may be the only gas conduit in the system. The first gas conduit may connect the first sample container to the first pressure actuator. The term "first gas conduit" is not intended to require the presence of additional gas conduits in the system.

The first compartment may include at least 2 sample conduits. The first compartment may include a first sample conduit and a second sample conduit.

The first compartment may include at least 4 connectors. The first compartment may include a first connector, a second connector, a third connector, and a fourth connector. These connectors may be referred to herein as interface-side connectors.

The first compartment may include a reagent conduit.

In some embodiments, the first sample conduit may be connected to the first sample container and the first connector. In some embodiments, the second sample conduit may be connected to the second sample container and the second connector. In some embodiments, the reagent conduit may be connected to the third and fourth connectors. In some embodiments, the first, second, third, and fourth connectors are disposed in the first, second, third, and fourth orifices, respectively. In some embodiments, the connectors and orifices serve to connect the sample containers to the interface.

In some embodiments of the described systems and methods, each sample container is connected to at least one gas conduit and at least one sample conduit.

The described second compartment may include a connector manifold. The connector manifold may include at least 4 connectors. The connector manifold may include a fifth connector, a sixth connector, a seventh connector, and an eighth connector. These connectors may be referred to herein as manifold-side connectors.

The second compartment may include a fractionation moiety. The fractionation moiety may be referred to as a first fractionation moiety. In some embodiments, the term first fractionation moiety does not necessarily indicate the presence of a second fractionation moiety. The fractionation moiety may be reversibly connected to the fifth sixth, and seventh connectors.

The second compartment may include a reagent container. The reagent container may be reversibly connected to the eighth connector.

Reference herein to reversible connection of a component, for example a container or fractionation moiety, to a connector, is not intended to imply a direct connection between the component and the connector. In some embodiments, a conduit may link the connector to the containers. In some embodiments, the connector may be a tube. The tube may be a polymer tube, non-limiting examples of which are polytetrafluoroethylene (PTFE), perfluoroalkoxy alkanes (PFA), fluorinated ethylene propylene (FEP), and nylons (linear polyamides). The tube may be stainless steel. In some embodiments, the conduit is directly and reversibly connected to the connector.

In some embodiments, the first connector may be connected to the fifth connector. In some embodiments, the second connector may be connected to the sixth connector. In some embodiments, the third connector may be connected to the seventh connector. In some embodiments, the fourth connector may be connected to the eighth connector. The connectivity may be similar to FIG. 1.

The described system may be configured to route the liquid sample from the first sample container to the fractionation moiety, and from the fractionation moiety to the second sample container. The described system may be configured to route a reagent from the reagent container to the fractionation moiety. In some embodiments, the aforementioned steps need not be the only process steps in a biochemical purification protocol. In some embodiments, the aforementioned steps may be preceded by additional steps. In some embodiments, the steps may be preceded by the step of transferring the sample to the first sample container. In some embodiments, the aforementioned steps may be followed by additional steps. In some embodiments, the steps may be both preceded and followed by additional steps.

In some embodiments, the first compartment of the described system may include a third sample container. The first compartment may optionally include a second pressure actuator.

The first compartment may include a second gas conduit. The second gas conduit may connect the second sample container to a pressure actuator. The actuator may be the first pressure actuator. The actuator may be the (optionally present) second pressure actuator. The actuator may be selected from the group consisting of the first pressure actuator and the second pressure actuator.

The first compartment may include a third sample conduit and a fourth sample conduit. The first compartment may include a ninth connector and a tenth connector. In some embodiments, the third sample conduit may be connected to the ninth connector. In some embodiments, the fourth sample conduit may be connected to the tenth connector.

The described second compartment may include an eleventh connector and a twelfth connector. These connectors may both be located in the connector manifold. The second compartment may also include a second fractionation moiety reversibly connected to the eleventh and twelfth connectors. Reference herein to a second fractionation moiety is not intended to require that the sample passes through the first fractionation moiety before passing through the second one. In some embodiments, the sample passes through the first fractionation moiety before the second one. In some embodiments, the sample passes through the second fractionation moiety before the first one.

The ninth and eleventh connectors may be connected to one another. The tenth and twelfth connectors may be connected to one another. The connectivity may be similar to FIG. 2A.

The described system may include at least 2 mass sensors. The mass sensors may each be configured to weigh a sample container associated therewith. The system may include a first mass sensor and a second mass sensor. The first and second mass sensors may be configured to weigh the first and second sample containers, respectively.

The described connectors may include an internal flanged tube component. In some embodiments, the first, second, third, and fourth connectors include an internal flanged tube component. In some embodiments, the first, second, third, fourth, ninth, and tenth connectors include an internal flanged tube component.

In some embodiments, a pulseless pump is present in the described first compartment. In some embodiments, an inline degasser is present. In some embodiments, the described system is configured to provide a hypobaric pressure environment to one or more sample containers. Such an environment can enable degassing of the sample, e.g., before loading it onto a chromatography column.

Pulseless pumps are known in the art, and are available commercially, for example under the trademarks DYNAPUMP® and Schwartzer Precision™.

Also provided herein is a method, in accordance with principles of the disclosure. The method may be a method for processing a liquid sample. The method may be a method for performing a biochemical purification protocol. The protocol may be a virus capsid purification protocol. The protocol may be another biochemical fractionation protocol. The protocol may be for processing a biological sample. The method may be automated.

The method may utilize an apparatus, the apparatus including a first compartment and a second compartment.

The first compartment may include an interface side. The first compartment may include at least 3 sample containers. The first compartment may include first, second, and third sample containers.

The second compartment may include a connector manifold.

The method may include the step of reversibly connecting a reagent container, a filtration apparatus, and a chromatography apparatus to the connector manifold. In some embodiments, the filtration apparatus may include a first (upstream) end and a second (downstream) end. In some embodiments, the chromatography apparatus may include a first (upstream) end and a second (downstream) end. The filtration apparatus may be a frontal-flow filtration apparatus. The filtration apparatus may be a tangential-flow filtration apparatus.

The method may include the step of reversibly connecting the interface side of the first compartment to the connector manifold.

The method may include the step of pressurizing the first sample container. The contents of the tank may be pressurized. The headspace of the tank may be pressurized.

The method may include the step of transferring at least a portion of the sample from the first sample container into the first end of the filtration apparatus. The sample may be routed via the described interface side and connector manifold. The sample may be routed from the first sample container, sequentially through the interface side and then the connector manifold, and into the first end of the filtration apparatus.

In this disclosure, reference may be made to a step of pressurizing a container, followed by a step of transferring a sample or reagent out of the container. In some embodiments, the step of pressuring serves to actuate the transfer of sample or reagent.

The method may include the step of passing at least a portion of the sample through a filter. The filter may be located within the filtration apparatus. The filter may be located between the first and second ends of the filtration apparatus.

The method may include the step of transferring at least a portion of the sample from the filtration apparatus into the second sample container. The sample may be transferred from the second end of the filtration apparatus into the second sample container. The sample may be routed via the connector manifold and the interface side. The sample may be routed from the filtration apparatus, sequentially through the connector manifold and the interface side, and into the second sample container.

The method may include the step of transferring at least a portion of the sample from the second sample container into the first end of the chromatography apparatus. The sample may be routed via the interface side and the connector manifold. The sample may be routed from the second sample container, sequentially through the interface side and the connector manifold, and into the chromatography apparatus.

The method may include the step of transferring the reagent from the reagent container into the chromatography apparatus. The sample may be routed via the first compartment. The sample may be routed via the connector manifold, the interface side, a reagent conduit in the first compartment, the interface side (again), and the connector manifold (again). The sample may be routed from the reagent container; sequentially through the connector manifold, the interface side, a reagent conduit, the interface side, and the connector manifold; and into the chromatography apparatus.

The reagent may be a mobile phase solvent. The reagent may be a mobile phase buffer. The reagent may be introduced into the upstream end of the chromatography apparatus, with respect to its direction of mobile phase flow.

The method may include the step of transferring at least a portion of the sample from the second end of the chromatography apparatus to the third sample container. The sample may be routed via the connector manifold and the interface side. The sample may be routed from the chromatography apparatus, sequentially through the connector manifold and the interface side, and into the third sample container.

In some embodiments, the aforementioned steps need not be the only process steps in a biochemical purification protocol. In some embodiments, the aforementioned steps may be preceded by additional steps. In some embodiments, the aforementioned steps may be followed by additional steps. In some embodiments, the aforementioned steps may be both preceded and followed by additional steps.

In some embodiments, the step of transferring the sample into the first end of the chromatography apparatus is performed at a substantially constant flow rate. In some embodiments, a pulseless pump is utilized for this purpose. In some embodiments, the method further includes the step of pressuring the third sample container, during the described transferring step into the chromatography apparatus.

In some embodiments, the described method includes the step of inline degassing a buffer utilized in the method. In some embodiments, the described method includes the step of inline degassing a reagent utilized in the method. In some embodiments, the described method includes the step of inline degassing a liquid sample. In some embodiments, the described method includes the step of inline degassing a buffer, reagent, or liquid sample.

In some embodiments, the described method further includes the step of reversibly connecting a sterile filter or filtration apparatus to the connector manifold. In some embodiments, the sterile filter may be attached to the same platform or connector manifold used for previous purification steps. In some embodiments, the second compartment associated with the platform may be used for multiple steps, including the sterile filtration step. In some embodiments, the sterile filter may be attached to a different platform from that used for one or more previous purification steps. In some embodiments, the platform used for the previous step(s) is detached when the step(s) are completed, and the sterile filtration apparatus is attached.

In some embodiments, the method further includes the step of passing at least a portion of the sample through the sterile filter. In some embodiments, sterile filtration is the final fractionation step. In some embodiments, sterile filtration is the final purification step. In some embodiments, sterile filtration is the final process step.

In some embodiments of the described method, the first compartment includes a fourth sample container.

In some embodiments, the method includes the step of reversibly connecting a tangential flow (TFF) filtration apparatus to the connector manifold. The TFF apparatus may include a tangential filter. The orientation of the filter may define a first and second end of the apparatus, wherein the tangential filter may extend from the first end to the second end. It will be appreciated by those skilled in the art that TFF direction is parallel to the filter, for example as illustrated in FIG. 2B. The TFF apparatus may be in addition to the aforementioned filtration and chromatography apparatus. In some embodiments, the method may utilize a frontal-flow filtration apparatus, a chromatography apparatus, and a TFF apparatus.

In some embodiments, the method includes the step of pressurizing the third sample container. In some embodiments, the method includes the step of transferring at least a portion of the sample from the third sample container into the first end of the tangential filtration apparatus. The sample may be routed via the interface side and the connector manifold. The sample may be routed from the third sample container, sequentially through the interface side and then the connector manifold, and into the first end of the tangential filtration apparatus.

In some embodiments, the method includes the step of transferring at least a portion of the sample from the first end to the second end of the tangential filtration apparatus.

In some embodiments, the method includes the step of transferring at least a portion of the sample from the second end of the tangential filtration apparatus to the fourth sample container. The sample may be routed via the connector manifold and the interface side. The sample may be routed from the tangential filtration apparatus, sequentially through the connector manifold and the interface side, and into the fourth sample container.

In some embodiments, the steps of transferring the sample from the third sample container, into and through the tangential filtration apparatus, and into the fourth sample container are all actuated by a pressure differential between the third and fourth tanks, wherein the third tank has a higher pressure.

In some embodiments, the method includes the step of pressurizing the fourth sample container. In some embodiments, the method includes the step of transferring at least a portion of the sample from the fourth sample container into the second end of the tangential filtration apparatus. The sample may be routed via the interface side and the connector manifold. The sample may be routed from the fourth tank, sequentially through the interface side and the connector manifold, and into the tangential filtration apparatus.

In some embodiments, the method includes the step of transferring at least a portion of the sample from the second end to the first end of the tangential filtration apparatus.

In some embodiments, the steps of transferring the sample from the fourth sample container into and through, the tangential filtration apparatus are all actuated by a pressure differential between the fourth and third tanks (sample containers), wherein the fourth tank has a higher pressure.

In some embodiments, the method includes the step of transferring at least a portion of the sample from the first end of the tangential filtration apparatus into the third sample container.

In some embodiments, the steps of transferring the sample from the fourth sample container, into and through the tangential filtration apparatus, and into the third sample container are all actuated by a pressure differential between the fourth and third tanks, wherein the fourth tank has a higher pressure.

In some embodiments of the described systems and methods, the steps of transferring the sample between the third and fourth tanks are performed iteratively. In some embodiments, these steps are performed a predetermined number of times. In some embodiments, these steps are performed until a predetermined concentration of a solution component has been reached, or is assessed to have been reached. In some embodiments, these steps are performed until a predetermined solution pH or conductivity has been reached, or is assessed to have been reached. In some embodiments, these steps are performed until a predetermined solution volume has been reached, or is assessed to have been reached. The aforementioned steps may serve to prepare the sample for a subsequent step wherein specified buffer characteristics are required. The aforementioned steps may serve to prepare the sample for a subsequent step wherein a specified product concentration or volume is required. The subsequent step may be a chromatography step. The subsequent step may be a final formulation.

In some embodiments of the described method, the third sample container is pressurized to a first pressure, and the fourth sample container is simultaneously (while the third container is pressurized) pressurized to a second pressure. In some embodiments, the first and second pressures are both greater than ambient pressure. In some embodiments, the first and second pressures alternate between the first pressure being greater than the second pressure vs. the second pressure being greater than the first pressure. In some embodiments, this arrangement enables bidirectional passage through a filtration apparatus under hyperbaric pressure. In some embodiments, the filtration system is a tangential filtration apparatus.

In some embodiments, the described method includes the step of monitoring the mass of the first sample container. In some embodiments, the method includes the step of monitoring the mass of the second sample container. In some embodiments, the method includes the step of monitoring the mass of the third sample container. In some embodiments, the method includes the step of monitoring the mass of the fourth sample container. Monitoring mass of sample containers may enable calculation of flow rates into and out of the containers, for example as described herein. It will be appreciated by those skilled in the art that the mass of a tank is the sum of the empty tank's mass and the mass of the contents. Since the empty tank's mass is constant, the flow rate of sample into or out of a tank can be calculated by the change in the full tank's mass. The calculation may utilize a processor. In some embodiments, the method includes the step of streaming mass data about a tank to a processor. In some embodiments, the method includes the step of calculating an actual flow rate from the tank. In some embodiments, the method includes the step of calculating an actual flow rate into the tank.

In some embodiments, the described method includes the step of predefining a desired flow rate from the second tank.

In some embodiments, the method includes the step of pressurizing the second sample container. In some embodiments, the headspace of the second tank is pressurized.

In some embodiments, the method includes the step of monitoring the mass of the second tank. In some embodiments, the method includes the step of streaming mass data about the second tank to a processor. In some embodiments, the method includes the step of calculating an actual flow rate from the second tank. In some embodiments, the method includes the step of dynamically adjusting the pressure of the second tank in order to achieve the desired flow rate. In some embodiments, the headspace pressure of the second tank is dynamically adjusted.

Also provided herein is a system, in accordance with principles of the disclosure. The system may include a first compartment and a second compartment. The second compartment may be reversibly connected to the first compartment. The second compartment may be reversibly connectable to the first compartment.

The first compartment may include an interface side. The interface side may include at least four orifices. The interface side may include a first orifice, a second orifice, a third orifice, and a fourth orifice. The interface side may include at least a first orifice, a second orifice, a third orifice, and a fourth orifice.

The first compartment may include at least 2 sample containers. The first compartment may include a first sample container and a second sample container. The first compartment may include at least a first sample container and a second sample container.

The first compartment may include at least 2 mass sensors. The mass sensors may each be configured to monitor mass of a sample container associated therewith. The first compartment may include a first mass sensor and a second mass sensor. The first compartment may include at least a first and a second mass sensor. The first and second mass sensors may be configured to monitor mass of the first and second sample containers, respectively.

The first compartment may include at least 2 sample conduits. The first compartment may include a first sample conduit and a second sample conduit. The first compartment may include at least a first and a second sample conduit.

The first compartment may include at least 4 connectors. The first compartment may include a first connector, a second connector, a third connector, and a fourth connector. The first compartment may include at least first, second, third, and fourth connectors. The first, second, third, and fourth connectors may be disposed in the first, second, third, and fourth orifices, respectively.

The first sample conduit may be connected to the first sample container and the first connector. The second sample conduit may be connected to the second sample container and the second connector.

The first compartment may include a reagent conduit. The reagent conduit may be connected to the third and fourth connectors.

The described second compartment may include a connector manifold. The connector manifold may include at least 4 connectors. The connector manifold may include a fifth connector, a sixth connector, a seventh connector, and an eighth connector. The connector manifold may include at least a fifth, a sixth, a seventh, and an eighth connector.

The described second compartment may include a fractionation moiety. The fractionation moiety may be referred to as a first fractionation moiety. The fractionation moiety may be reversibly connected to the fifth sixth, and seventh connectors. The fractionation moiety may be a first fractionation moiety among a plurality of fractionation moieties. The fractionation moiety may be the only fractionation moiety. The term first fractionation moiety is not intended to convey that additional fractionation moieties are present in the system.

The fractionation moiety may be a filtration apparatus. The moiety may be a chromatography apparatus. Both types of fractionation moieties may be present in the system.

The described second compartment may include a reagent container. The reagent container may be reversibly connected to the eighth connector.

In some embodiments, the first and fifth connectors may be joined to one another. In some embodiments, the second and sixth connectors may be joined to one another. In some embodiments, the third and seventh connectors may be joined to one another. In some embodiments, the fourth and eighth connectors may be joined to one another. The connectivity may be similar to FIG. 1.

In some embodiments, the described system may be configured to route the liquid sample from the first sample container to the fractionation moiety, and from the fractionation moiety to the second sample container. The described system may be configured to route a reagent from the reagent container to the fractionation moiety.

In some embodiments, the aforementioned steps need not be the only process steps in a biochemical purification protocol. In some embodiments, the aforementioned steps may be preceded by additional steps. In some embodiments, the aforementioned steps may be followed by additional steps. In some embodiments, the aforementioned steps may be both preceded and followed by additional steps.

In some embodiments, the described connectors may include an internal flanged tube component. In some embodiments, the first, second, third, and fourth connectors include an internal flanged tube component. In some embodiments, the first, second, third, fourth, ninth, and tenth connectors include an internal flanged tube component.

In some embodiments, the described first compartment includes a third sample container and a third mass sensor. The third mass sensor may be configured to monitor the mass of the third sample container.

In some embodiments, the described first compartment includes at least 4 sample conduits. In some embodiments, the first compartment includes third and fourth sample conduits. In some embodiments, the first compartment includes at least a third and fourth sample conduit.

In some embodiments, the described first compartment includes a ninth connector and a tenth connector. In some embodiments, the first compartment includes at least a ninth and tenth connector, in addition to the first, second, third, and fourth mentioned hereinabove.

In some embodiments, the described second compartment includes an eleventh connector and a twelfth connector. In some embodiments, the second compartment includes at least an eleventh and twelfth connector, in addition to the fifth, sixth, seventh, and eighth connectors described hereinabove. The eleventh and twelfth connector may be both disposed in the connector manifold.

In some embodiments, the described second compartment includes a second fractionation moiety. The second fractionation moiety may be reversibly connected to the eleventh and twelfth connectors.

The ninth and eleventh connectors may be joined to one another. The tenth and twelfth connectors may be joined to one another. The connectivity may be similar to FIG. 2A.

In some embodiments, a pulseless pump is present in the described first compartment. In some embodiments, an inline degasser is present.

Also provided herein is a method, in accordance with principles of the disclosure. The method may utilize an apparatus, the apparatus including a first compartment and a second compartment. The first compartment may include an interface side and at least 3 sample containers. The first compartment may include a first, second, and third sample container. The first compartment may include at least a first, second, and third sample container. The second compartment may include a connector manifold. The method may be automated.

The described method may include the step of reversibly connecting a reagent container, a filtration apparatus, and a chromatography apparatus to the connector manifold. First (upstream) and second (downstream) ends may be recognizable in both the filtration apparatus and the chromatography apparatus. The filtration apparatus may be a frontal flow filtration apparatus. The filtration apparatus may be a tangential flow filtration apparatus.

The first and second ends of a described filtration apparatus may be defined with respect to one or more filters within the apparatus. In the case of a frontal flow apparatus, the first and second ends may be defined as being located on opposite sides of the filter, such that a sample originating on the first end must pass through the filter in order to arrive at the second end.

The first and second ends of a described chromatography apparatus may be defined with respect to a column within the apparatus. The first and second ends may be defined as being located on opposite ends of the column, such that a sample originating on the first end must pass through the column in order to arrive at the second end.

The described method may include the step of reversibly connecting the interface side of the first compartment to the connector manifold.

The described method may include the step of transferring at least a portion of the sample from the first sample container into the first end of the filtration apparatus. The sample may be transferred via the interface side and the connector manifold. The sample may be transferred from the first sample container, sequentially through the interface side and the connector manifold, and into the filtration apparatus.

The described method may include the step of monitoring mass of the first sample container. Monitoring mass of the tank may enable calculation of the flow rate. Monitoring mass of the tank may enable calculation of the amount of sample transferred out of the tank.

The described method may include the step of passing at least a portion of the sample through a filter located within the filtration apparatus. The filter may be located between the aforementioned first and second ends of the filtration apparatus.

The described method may include the step of transferring at least a portion of the sample from the filtration apparatus into the second sample container. The sample may be transferred via the connector manifold and the interface side. The sample may be transferred from the filtration apparatus, sequentially through the connector manifold and the interface side, and into the second tank.

The described method may include the step of monitoring mass of the second sample container. Monitoring mass of the tank may enable calculation of the flow rate. Monitoring mass of the tank may enable calculation of the amount of sample transferred out of the tank.

The described method may include the step of monitoring mass of the third sample container. Monitoring mass of the tank may enable calculation of the flow rate. Monitoring mass of the tank may enable calculation of the amount of sample transferred out of the tank.

The described method may include the step of transferring at least a portion of the sample from the second tank into the first end of the chromatography apparatus. The sample may be transferred via the interface side and the connector manifold. The sample may be transferred from the second tank, sequentially through the interface side and the connector manifold, and into the chromatography apparatus.

The described method may include the step of transferring the reagent from the reagent container into the chromatography apparatus. The sample may be transferred via the first compartment. The sample may be transferred via the connector manifold, the interface side, a reagent conduit, the interface side, and the connector manifold. The sample may be transferred from the reagent container, sequentially through the interface, a reagent conduit, and the interface (again), and into the chromatography apparatus. The reagent may be a chromatography buffer. The reagent may be a mobile phase solvent. The reagent may be a mobile phase buffer. The reagent may be introduced into the upstream end of the chromatography apparatus, with respect to its direction of motion during the chromatography process.

The described method may include the step of transferring at least a portion of the sample from the first end to the second end of the chromatography apparatus.

The described method may include the step of transferring at least a portion of the sample from the second end of the chromatography apparatus to the third sample container. The sample may be transferred via the connector manifold and the interface side. The sample may be transferred from the chromatography apparatus, sequentially through the connector manifold and the interface side, and into the third tank.

In some embodiments of the described method, the step of transferring the sample into the first end of the filtration apparatus may be performed at a substantially constant pressure differential between the first and second sample containers.

In some embodiments of the described method, the step of transferring the sample into the first end of the chromatography apparatus may be performed at a substantially constant flow rate. In some embodiments, a pulseless pump is utilized for this purpose. In some embodiments, the method may include the step of pressuring the third sample container, during the transfer of the sample into the first end of the chromatography apparatus.

In some embodiments, the described method includes the step of inline degassing a buffer utilized in the method. In some embodiments, the described method includes the step of inline degassing a reagent utilized in the method. In some embodiments, the described method includes the step of inline degassing a liquid sample. In some embodiments, the described method includes the step of inline degassing a buffer, reagent, or liquid sample.

In some embodiments, the method includes the step of reversibly connecting a tangential flow filtration (TFF) apparatus to the connector manifold. The TFF apparatus may include a tangential filter. The orientation of the filter may define a first and second end of the apparatus, wherein the tangential filter may extend from the first end to the second end.

The TFF apparatus may be in addition to the aforementioned filtration and chromatography apparatus. In some embodiments, the method may utilize a frontal-flow filtration apparatus, a chromatography apparatus, and a TFF apparatus. In some embodiments, product is run through the frontal-flow filtration apparatus before the chromatography apparatus, and then the TFF apparatus. In some embodiments, additional prior method steps are performed. In some embodiments, additional subsequent method steps are performed. In some embodiments, additional prior and subsequent method steps are performed.

In some embodiments, the method includes the step of pressurizing the third sample container. In some embodiments, the method includes the step of transferring at least a portion of the sample from the third sample container into the first end of the TFF apparatus. The sample may be routed via the interface side and the connector manifold. The sample may be routed from the third sample container, sequentially through the interface side and then the connector manifold, and into the first end of the tangential filtration apparatus.

In some embodiments, the method includes the step of transferring at least a portion of the sample from the first end to the second end of the tangential filtration apparatus.

In some embodiments, the method includes the step of transferring at least a portion of the sample from the second end of the tangential filtration apparatus to the fourth sample container. The sample may be routed via the connector manifold and the interface side. The sample may be routed from the tangential filtration apparatus, sequentially through the connector manifold and the interface side, and into the fourth sample container.

In some embodiments, the steps of transferring the sample from the third sample container, into and through the tangential filtration apparatus, and into the fourth sample container are all actuated by a pressure differential between the third and fourth tanks, wherein the third tank has a higher pressure.

In some embodiments, the method includes the step of pressurizing the fourth sample container. In some embodiments, the method includes the step of transferring at least a portion of the sample from the fourth sample container into the second end of the tangential filtration apparatus. The sample may be routed via the interface side and the connector manifold. The sample may be routed from the fourth tank, sequentially through the interface side and the connector manifold, and into the tangential filtration apparatus.

In some embodiments, the method includes the step of transferring at least a portion of the sample from the second end to the first end of the tangential filtration apparatus.

In some embodiments, the steps of transferring the sample from the fourth sample container into and through the tangential filtration apparatus are all actuated by a pressure differential between the fourth and third tanks, wherein the fourth tank has a higher pressure.

In some embodiments, the method includes the step of transferring at least a portion of the sample from the first end of the tangential filtration apparatus into the third sample container.

In some embodiments, the steps of transferring the sample from the fourth sample container, into and through the tangential filtration apparatus, and into the third sample container are all actuated by a pressure differential between the fourth and third tanks, wherein the fourth tank has a higher pressure.

In some embodiments of the described method, the third sample container is pressurized to a first pressure, and the fourth sample container is pressurized to a second pressure while the third container remains pressurized. In some embodiments, the first and second pressures are both greater than ambient pressure. In some embodiments, the first and second pressures alternate between the first pressure being greater and the second pressure being greater.

In some embodiments, the described method includes the step of pressurizing the first, second, third, and/or fourth sample containers. As provided herein, tank pressurization can be used to actuate movement of fluids out of the pressurized tank.

In some embodiments, the described method includes the step of predefining a desired flow rate from the first, second, and/or third tank. In some embodiments, the method includes the step of monitoring the mass of the tank of interest. In some embodiments, the method includes the step of streaming mass data about the tank to a processor. In some embodiments, the method includes the step of calculating an actual flow rate from the tank. In some embodiments, the method includes the step of dynamically adjusting the pressure of the tank in order to achieve the desired flow rate. In some embodiments, the headspace pressure of the tank is dynamically adjusted. In some embodiments, the processor may be configured to generate, or create, an audit trail. The audit trail may include a record of the sequence and timing of fluid transfers within the system.

Reference herein to a "first" compartment is not intended to limit the disclosure to systems wherein the named first compartment temporally handles the sample before the named second compartment. Rather, the terms "first" and "second", for example when referring to compartments, are intended to serve the purpose of enabling separate referencing of different system compartments, without implying a particular temporal progression.

Reference herein to a "first" component, for example a first orifice, sample container, gas conduit, sample conduit, or connector, is not intended to limit the disclosure to systems wherein the named first component temporally handles the sample before the named second component. Rather, the terms "first" and "second", for example when referring to any components, are intended to serve the purpose of enabling separate referencing of different system components, without implying a particular temporal progression.

Reference herein to a "gas conduit" or "liquid conduit" is not intended to require that the conduit be designated only for movement of gas or liquid (as appropriate). In some embodiments, each conduit is suitable for both gases and liquids. In some embodiments, the disclosure encompasses systems and methods wherein a given conduit is used for both a gas and a liquid in the same process. In some embodiments, a gas, for example pressurized air, may be used to flush a line after liquid transfer, to increase transfer yield.

Reference herein to a sample is intended to encompass any sample that is handled by a described process and/or in a described system, regardless of its stage of purification.

In some embodiments of the described methods and systems, a tank is partially filled with fluid, leaving a headspace in the tank. In some embodiments, a pressure inlet is situated in order to direct incoming pressure to the headspace. In some embodiments, the pressure inlet faces the tank's headspace. In some embodiments, the pressure inlet is located in the upper 30% of the tank's vertical dimension (height). In some embodiments, the pressure inlet is located in the upper 20% of the tank's vertical dimension. In some embodiments, a tank is pressurized before introduction of sample into the tank. In some embodiments, a tank is pressurized while no fluid is present in the tank. Pressurizing a tank that does not contain fluid can server, in some embodiments, to provide back pressure for a purification process requiring hyperbaric pressures, a non-limiting example of which is tangential flow filtration. In some embodiments, hyperbaric pressure serves to prevent degassing of fluids during column chromatography. In some embodiments, hyperbaric pressure serves to deter entry of external contaminants.

In some embodiments, an outlet to a sample conduit is located in the lower 20% of the tank's vertical dimension (height). In some embodiments, an outlet is located in the lower 10% of the tanks' vertical dimension.

In some embodiments of the described methods and systems, the second compartment does not contain any pumps. In some embodiments, the second compartment does not contain any sensors. In some embodiments, the second compartment does not contain any pressure actuators. In some embodiments, the second compartment does not contain any pumps, sensors, or pressure actuators.

In some embodiments of the described methods and systems, the first compartment may be fixedly connected to supplies of gases (e.g., compressed air), steam, and/or cleaning fluids. In some embodiments, the second (or "peripheral") compartment(s) is not fixedly connected to any supplies of gases (e.g., compressed air), steam, and/or cleaning fluids. Fixedly may refer to a connection not intended to be disassembled and assembled on an ongoing basis, as will be appreciated by those skilled in the art.

In some embodiments of the described methods and systems, the first compartment may be fixedly connected to one or more utility lines or conduits which contain or supply air and/or a cleaning medium (e.g., a cleaning fluid). The first compartment may be connected to additional lines which contain or supply additional compartments, for example water, diluting buffers, etc. In certain embodiments, the additional lines supply 2 or more components selected from ambient air, carbon dioxide, steam, purified water, and cleaning solution. In other embodiments, 3 or more of the aforementioned components, 4 or more of the aforementioned components, or all 5 of the aforementioned components are supplied to the first compartment by lines to which the component is connected. In some embodiments, the connection is a fixed connection. In some embodiments, the first compartment is not fixedly connected to utility lines or conduits.

In some embodiments of the described methods and systems, the first compartment includes at least one pH sensor. In some embodiments, the pH sensor is located in a fluid path between a separation moiety and a destination product container. In some embodiments, a described method includes the step of monitoring pH during a purification step. In some embodiments, pH is monitored prior to initiating a purification step. In some embodiments, process parameters are adjusted in response to pH readings. In some embodiments, a single pH sensor is used for monitoring pH during multiple purification steps.

In some embodiments, the first compartment includes at least one pressure sensor. In some embodiments, the pressure sensor is located in a fluid path between a separation moiety and a destination product container. In some embodiments, a described method includes the step of monitoring pressure during a purification step. In some embodiments, pressure is monitored prior to initiating a purification step. In some embodiments, process parameters are adjusted in response to pressure readings. In some embodiments, a single pressure sensor is used for monitoring pressure during multiple purification steps.

In some embodiments of the described methods and systems, at least one (additional) incoming gas conduit connects the connector manifold to a reagent container. The incoming gas conduit may connect, via the connector manifold and the interface, to an additional (outgoing) gas conduit from a pressure actuator in the first compartment. In some embodiments, pulses of a gas, for example compressed air, can be used to actuate movement of a reagent on the side of the second compartment.

In some embodiments of the described methods and systems, at least one additional sample conduit directly connects two sample containers to one another. In some embodiments, pressure exerted on a first sample container can actuate movement of the sample directly into a second tank.

In some embodiments, the described first compartment is configured to connect a chromatography apparatus to a buffer or solvent container that is attached to the second compartment, while the column is dripping. In some embodiments, the drop-to-drop method is utilized. In some embodiments, the first compartment may be configured to equilibrate a column, prior to a described biochemical purification method. In some embodiments, following a described biochemical purification method, the first compartment may be configured to chemically clean a column while the first compartment remains attached to the second compartment. In some embodiments, following chemical cleaning of a column, the first compartment may be configured to flush out the cleaning solution, while the first compartment remains attached to the second compartment. In some embodiments, these procedures may serve to prepare the column for a future procedure.

In some embodiments, following a described biochemical purification method, the first compartment may be configured to chemically clean a filter while the first compartment remains attached to the second compartment. In some embodiments, following chemical cleaning of a filter, the first compartment may be configured to flush out the cleaning solution, while the first compartment remains attached to the second compartment. In some embodiments, these procedures may serve to prepare the filter for a future procedure.

In some embodiments, the described system includes 7 sample containers. The containers may be configured to perform the steps of membrane filtration-mediated clarification, diafiltration via tangential flow filtration (TFF), affinity chromatography, an additional TFF, ion-exchange (IEX) chromatography, a third round of TFF, and sterile filtration.

In some embodiments, a described method includes the steps of membrane filtration-mediated clarification, diafiltration via TFF, affinity chromatography, an additional TFF, IEX chromatography, a third round of TFF, and sterile filtration. In some embodiments, the aforementioned steps are performed in the mentioned order. In some embodiments, each round of TFF serves to adapt the buffer composition and/or volume to the requirements of the subsequent step. In some embodiments, the method is a virion purification method.

In some embodiments, the system enables an option of either a fixed pressure differential flow or a constant rate flow. In some embodiments, the system enables both fixed pressure differential flow and constant rate flow to be used for different process stages. In some embodiments, a fixed pressure differential flow may be used for filtration. The filtration may have a maximum recommended differential pressure. In some embodiments, a constant rate flow may be used for chromatography. The chromatography may have a recommended column loading rate.

In some embodiments, a fixed differential pressure may be achieved by dynamically regulating each tank's headspace pressure. In some embodiments, a constant rate flow may be achieved by using a pulseless pump. In some embodiments, dynamic regulation of tank headspace pressures is used in tandem with a pulseless pump to provide a constant rate flow against a selectable back pressure.

In some embodiments, membrane filtration clarification utilizes increasingly fine membranes. Solely for exemplification, the membranes could have pore sizes of (5 microns, 1 micron, and 0.45 microns. This step may serve to remove any particulate matter greater than the finest filter used. Such matter may include cellular debris.

In some embodiments, a method of diafiltration via TFF includes passing a sample back and forth across a membrane under hyperbaric pressure. The membrane may be sufficiently fine to only allow liquids and particulates smaller than the target product to pass through. This step may adapt the salt concentration and pH to appropriate levels for chromatography.

In some embodiments, an affinity chromatography step utilizes an affinity chromatography column to which the product selectively binds. Wash buffer and impurities may pass through the column to a waste container. Subsequently an elution buffer may be added, which may release the product from the column to a tank for further processing.

In some embodiments, a round of diafiltration via TFF, following affinity chromatography, replaces the buffer with one suitable for an IEX column.

In some embodiments, IEX chromatography may serve to separate capsids containing nucleic acid from unfilled capsids. In some embodiments, this step may utilize a gradual transition from wash to elution buffer. In some embodiments, this step may utilize UV sensors to monitor the column output. In some embodiments, readings from the UV sensors are used to determine which fraction should be selected for further processing. UV may be measured at multiple wavelengths to give reading of both protein and nucleic acid quantities of each fraction. In some embodiments, isocratic wash and elution steps are used to release the empty and full capsids.

In some embodiments, the third round of diafiltration via TFF replaces the buffer with one suitable for storage. In some embodiments, this diafiltration brings the product to the desired concentration.

In some embodiments, sterile filtration is achieved by passage through a sterile filter. In some embodiments, sterile filtration is followed by transfer to an external fill and finish station, which is used to dose and package the product.

As used herein, the term connector manifold may refer to any structure that includes multiple connectors. The manifold may have a substantially planar surface. The manifold may include a contiguous block. The interface side of the first compartment may also include a connector manifold, which may include any of these characteristics.

Reference herein to a flanged tube component is intended to encompass any suitable flanged tube. In some embodiments, the flanged tube is connected to the interface side of the first component.

In some embodiments of the described methods and systems, a new second compartment is attached to the first compartment before a new step in the purification process is initiated. Such steps may include, for example, a filtration step or a chromatography step. In some embodiments, the previous second compartment is detached prior to attaching the new second compartment. Use of a different second compartment for each purification step may provide process flexibility. Use of a different second compartment for each purification step may enable use of labile components in the process. Use of a different second compartment for each purification step may enable relatively precise control of parameters such as temperature and pH for solutions utilized in the process.

In some embodiments, one second compartment is utilized for multiple purification steps. In some embodiments, the second compartment remains attached to the first compartment while the multiple steps are running.

In some embodiments of the described systems and methods, each gas conduit is connected to a source of pressurized gas. The gas may be air. The source may be a pressure actuator. The source may be a pressure pump. The source may be selected from the group consisting of a pressure actuator and a pressure pump. In some embodiments, the described pressure actuator(s) are pressure regulator(s). In some embodiments, a pressure regulator is used as a pressure source in the described methods. The pressure regulator may be programmatically set to a predetermined pressure level by a controller. If the set pressure level is greater than the pressure in a proximal air line, which is disposed downstream relative to the actuator, pressured air may flow through the proximal air line.

Filtration and chromatography are known techniques in virus capsid purification and other biotechnological processes. Their use is described, for example by Adams B et al. (Moving from the bench towards a large scale, industrial platform process for adeno-associated viral vector purification. Biotechnol. Bioeng. 2020, 117, 3199-3211), Srivastava A et al. (Manufacturing challenges and rational formulation development for AAV viral vectors. J. Pharm. Sci. 2021, 110, 2609-2624), Hillebrandt N et al. (Integrated Process for Capture and Purification of Virus-Like Particles: Enhancing Process Performance by Cross-Flow Filtration. Front. Bioeng. And Biotechnol. 2020, 8; https://doi.org/10_3389/fbioe.2020.00489), and other references.

As used herein, filtration may refer to passage over a membrane that selects components on the basis of size and/or other parameters.

As used herein, chromatography may refer to passage through a substrate or column that selects components on the basis of size, affinity to column components, ionic charge, or other characteristics. Non-limiting examples of chromatography are size-exclusion chromatography, affinity chromatography, ion-exchange chromatography, and mixed-mode chromatography.

Reference herein to a liquid sample is intended to encompass any biological material in liquid form. In some embodiments, the sample may be a cell supernatant. In some embodiments, the liquid sample may be a cell lysate.

In some embodiments of the described systems and methods, the second compartment of the described system has an identical configuration to the second compartment of the upstream apparatus. Systems including downstream and upstream apparatuses are described hereinbelow.

In some embodiments, any of the described sample containers is not filled more than 80%, in order to provide headspace for pressurization.

In some embodiments, the pressurized gas used in the described systems and methods is selected from the group consisting of ambient air, nitrogen, oxygen, helium, carbon dioxide, and a mixture thereof. In some embodiments, the gas has been filtered to remove particulate matter.

In some embodiments, there is provided herein a system, in accordance with principles of the disclosure, including an upstream apparatus and a downstream apparatus. The upstream apparatus may be configured for biotechnological processes involving living cells. The upstream apparatus may include a feature described hereinbelow. The downstream apparatus may be configured for biochemical purification procedures. The downstream apparatus may correspond to any of the aforementioned systems for biochemical purification. The downstream apparatus may include any of the features described hereinabove.

In some embodiments, the upstream and downstream apparatuses may be within a single housing. In other embodiments, the first and second apparatuses may be enclosed in separate housings. In either case, the 2 apparatuses may share utilities, for example pressure actuators, utility lines, or the like.

Also provided is a method for incubating living cells and isolating a product of the cells, in accordance with principles of the disclosure. The method may include the steps of incubating and lysing virus-producing cells, for example using an upstream apparatus as described herein. The method may also include the step of biochemically purifying the product, for example using a downstream apparatus as described herein.

In some embodiments, the aforementioned embodiments of biochemical purification systems and methods may be applicable to the upstream apparatus.

Upstream Apparatuses and Methods

In an exemplary upstream process, a bioreactor may be populated with cells, which grow and divide under controlled conditions. Cells may be used to produce a molecule of interest or other product, e.g., recombinant virus particles. The bioreactor may be stirred and may contain sensors for pH, dissolved oxygen, and temperature, which are used to trigger additions of acid, base, air, carbon dioxide, and warming, to maintain optimum cell health in culture. These additions may be performed using pressurized air-driven flow, as described herein.

An upstream apparatus in accordance with principles of the disclosure may include a central compartment or component and a peripheral compartment or component. The central compartment may include, and/or be at least partially bounded by, an interface, which may be referred to as a central-side interface, via which the central compartment interacts with the peripheral compartment. The apparatus may be configured for cell culture. The cell culture may be for the purpose of virus production. The cell culture may be for the purpose of cell harvesting. The apparatus may be configured for other biotechnological processes known to those skilled in the art.

The terms central and peripheral, when referring to compartments of the upstream apparatus, do not necessarily imply centrality or peripherality with regard to a particular central landmark or vantage point. In some embodiments, the central compartment(s) may be fixed (e.g., floor mounted or wall mounted), while the peripheral compartment(s) may be portable. The peripheral compartment(s) may be moved or toggled between one or more central compartments, reuse compartments, or the like, by detaching it/them (if attached), moving it/them to a different fixed compartment, and attaching it/them to the new fixed compartment. This process may be largely or fully automated. In some embodiments, the peripheral compartment(s) may be supported by a shelf or portable cart configured for such use.

The central compartment of the upstream apparatus may also include: (i) one or more pressure actuators; (ii) multiple outgoing pressure lines connecting the one or more pressure actuators to the central-side interface; (iii) a bioreactor chamber; and (iv) a plurality of incoming fluid lines connecting the central-side interface to the bioreactor chamber. The bioreactor chamber may be configured to house the living cells and a growth medium.

The peripheral compartment of the upstream apparatus may include: (i) multiple fluid storage containers; (ii) multiple incoming pressure lines; and (iii) multiple outgoing fluid lines. Each fluid storage container may operably connected to at least one incoming pressure line and at least one outgoing fluid line, which means, in some embodiments, that an incoming pressure line can be used to exert pressure on the interior of the fluid storage container to which it is connected, and an outgoing fluid line can be used to convey fluid out of the fluid storage container to which it is connected. When connected, an impetus originating from the pressure actuator(s) (which may be conveyed by pressure) may serve to move fluid (e.g., buffers and other fluids required for cell incubation, cell suspensions, a virus inoculum, and the like) from reagent tanks or container in the peripheral compartments into the bioreactor chamber. The amounts of reagents moved may be predetermined according to a set program. Non-limiting examples of fluids that may be present in the fluid storage contains are buffers (e.g., bicarbonate), anti-foaming agents, and other fluids required for cell incubation; a cell suspension, a virus inoculum, a lysis reagent, and a nuclease (non-limiting examples of which are endonucleases sold under the trade name Benzonase®). The amounts of reagents moved may be predetermined according to a set program.

In some embodiments, the central compartment of the upstream apparatus may include filters that are configured to deliver a sterile gas (e.g, air) in pressurized form through one of 2-3 interfaces into tanks. The pressure may impel fluid to flow from the tanks into the bioreactor. In additional embodiments, the central compartment may be configured to reverse the air flow for sampling from the bioreactor. The central compartment may supply air through sterile filters into the bioreactor, moving fluid from the reactor across one of the interfaces and into a sample tank disposed in a described peripheral compartment. In some embodiments, the central compartment may be configured to support steaming, monitoring, and testing of any of the herein-described components. In some embodiments, use of a pressurized gas reduces mechanical failure modes.

In some embodiments, the described pressure actuator(s) are pressure regulator(s). In some embodiments, a pressure regulator is used as a pressure source in the described methods. The pressure regulator may be programmatically set to a predetermined pressure level by a controller. If the set pressure level is greater than the pressure in a proximal air line, which is disposed downstream relative to the actuator, pressured air may flow through the proximal air line. The filter may be operably connected to a vent, a drain, a pressure sensor, and a temperature sensor. In some embodiments, pressurized air proceeds through a sterile air line downstream of the filter to a headspace of a reagent container, which may be, in some embodiments, a medium reservoir or a reservoir of another liquid reagent (e.g., a reagent needed for a biotechnological process). In some embodiments, increased pressure in the headspace impels an amount, which may be predetermined amount, of the container's fluid contents out of the container, through a downstream fluid line, and into a fluid destination container.

In some embodiments, the outgoing pressure lines lead from the pressure actuators to the interface and are configured to transmit pressure from the pressure actuators to their termini in the central-side interface. To this end, the pressure actuator(s) may be operably connected with the outgoing pressure lines.

In some embodiments, the incoming fluid lines lead from the interface to the bioreactor chamber and are configured to transport fluid originating in fluid storage containers from the central-side interface to the bioreactor chamber.

In some embodiments, the central compartment of the upstream apparatus may be configured for cleaning, sterilization and reuse. For example, it may be possible to clean sterilize the central compartment (e.g., as described herein) and subsequently use it for additional incubations.

Each of the incoming pressure lines may be configured to sterilely and reversibly connect to one of the outgoing pressure lines. In some embodiments, the connection is via a described interface. In some embodiments, the apparatus is configured for connection and disconnection of interfaces to be largely, or fully, automated.

Sterilely may refer to a connection that excludes access of microbes to the interior of the mentioned lines. Reversibly may refer to a connection that can be dismantled, while preserving the structure of the mentioned lines and their ability to be cleaned and reused in a sterile, closed system.

Returning to the central compartment, the central compartment may include a combination of sensors and/or valves. The sensors may include scales that serve as fluid sensors. In some embodiments, the fluid sensors may be configured to monitor fluid transfers within the system. In some embodiments, the valves may be associated with any of the described fluid lines; for example, the incoming fluid lines. In some embodiments, the valves may be configured to prevent retrograde movement of fluid within the system. In some embodiments, a processing unit may be operably connected to the fluid sensors. The processing unit may be configured to generate, or create, an audit trail. The audit trail may include a record of the sequence and timing of fluid transfers within the system.

The bioreactor chamber may be made of stainless steel and may, in some embodiments, be reusable. The bioreactor chamber may be made of glass and may, in some embodiments, be reusable. In some embodiments, the bioreactor chamber may be made of plastic and may, in some embodiments, be disposable. In some embodiments, the bioreactor chamber may be made of plastic and may, in some embodiments, be reusable.

In some embodiments, each of the outgoing pressure lines and incoming fluid lines includes a terminus, collectively referred to as central-side termini. The central-side termini may be arranged in a first essentially planar array, which is, in some embodiments, disposed in the central-side interface. The central-side interface may be configured to mate with, or be juxtaposed to, a peripheral-side interface having a corresponding spatial arrangement, e.g., a mirror image of the central-side interface.

In some embodiments, each of the incoming pressure lines and outgoing fluid lines includes a terminus, collectively referred to as peripheral-side termini. The peripheral-side termini may be arranged in a second essentially planar array, which is, in some embodiments, disposed in a peripheral-side interface. The peripheral-side interface may be configured to mate with, or be juxtaposed to, the central-side interface.

Each of the central-side termini may be configured to mate, or connect, with a corresponding peripheral-side terminus. The interface or connector may be configured to consummate the connection in a multi-step process, for example, including the steps of (a) enclosing the termini within an enclosure resistant to pathogen entry; (b) sterilizing the interior of the enclosure; and (c) fluidly connecting the termini pairs. Sterility of the enclosure may be maintained until step (c) is completed. Step (a) may be preceded by juxtaposing (but not yet fluidly connecting) the corresponding terminus pairs. In some embodiments, each enclosure contains individual pairs of termini. In some embodiments, an enclosure encompasses multiple pairs of termini.

The central compartment may be connected to one or more utility lines or conduits which contain or supply air, a sterilizing medium (e.g., a sterilizing gas) and/or a cleaning medium (e.g., a cleaning fluid). The central compartment may be connected to additional lines which contain or supply additional compartments, for example water, diluting buffers, etc. In certain embodiments, the additional lines supply 2 or more components selected from ambient air, carbon dioxide, steam, purified water, and cleaning solution. In other embodiments, 3 or more of the aforementioned components, 4 or more of the aforementioned components, or all 5 of the aforementioned components are supplied to the central compartment by lines to which the component is connected. In some embodiments, the connection is a fixed connection. Fixed may refer to a connection not intended to be disassembled and assembled on an ongoing basis, as will be appreciated by those skilled in the art.

Those skilled in the art will appreciate that a non-limiting list of sterilizing media includes steam, dry heat, ethylene oxide, vaporized hydrogen peroxide, chlorine dioxide gas, vaporized peracetic acid, and nitrogen dioxide. The sterilizing medium may be a gas, e.g., a heated gas. The sterilizing medium may be steam.

The cleaning medium may be a cleaning fluid. The cleaning fluid may include detergents or surfactants (for example, anionic detergents or cationic detergents). Solutions of acids (e.g., citric acid, hydrochloric acid, or acetic acid) or bases (e.g., NaOH) may also be used as cleaning solutions.

The central compartment may additionally include a pressure-driven (or pressurized) product sampling line or conduit, connecting the bioreactor chamber to a sample container. The sampling line may lead from the bioreactor chamber to the sample container and be configured to transfer a sample from the bioreactor chamber to the sample container. In some embodiments, the sample container is disposed in the central compartment. In some embodiments, the sample container is disposed in the peripheral compartment. Sampling may be conducted at multiple intervals, as necessary to monitor one or more environmental conditions, cell metabolite levels or production milestones. Any of the former may be used to inform process adjustments, for example pH adjustment, medium replenishment, or product harvesting.

In some embodiments, differential pressure is used to impel the sample out of the chamber. In some embodiments, the bioreactor is operably connected to a positive pressure line configured to impel a sample out of the bioreactor, as described generally herein for fluid movement via pressurized air. In other embodiments, the sample container is operably connected to a negative pressure, or vacuum, line, which may create negative pressure in the interior of the sample container, thereby drawing a sample from the bioreactor chamber to the sample container.

In some embodiments, the peripheral compartment (or an additional peripheral compartment, if more than one is utilized) also includes a virus container, a third incoming pressure line connected to the virus container, and a third outgoing fluid line connected to the virus container. In other embodiments, a polynucleotide container, containing a polynucleotide solution, is present instead of a virus container. In other embodiments, a polynucleotide container, containing a polynucleotide solution, is present in addition to a virus container, either in the same peripheral compartment (e.g., in different containers) or in a different peripheral compartment. A corresponding outgoing pressure line(s) and an incoming fluid line(s) may be present in the central compartment and configured to mate with the virus and/or polynucleotide container-associated lines. In some embodiments, the polynucleotide is a vector required for the desired biotechnological process.

In some embodiments, the pressurized gas used in the upstream apparatus is a biologically compatible gas, for example nitrogen, oxygen, carbon dioxide, or a mixture thereof. In some embodiments, the pressurized gas is ambient air. In some embodiments, the pressurized gas is sterile filtered, for example sterile-filtered air. In some embodiments, the filters have been sterilized (e.g., via steam), and filter integrity has been tested, prior to commencing the described method.

In some embodiments, the filters impel air through one of 1-3 interfaces into reagent containers or tanks, which in turn drives fluid to flow into the bioreactor. In some embodiments, the sampling process uses a reverse air flow path. Air may be supplied through sterile filters into the bioreactor, moving fluid from the reactor across one of the interfaces and into a sample tank.

In some embodiments, the method further includes the step of monitoring the mass of the bioreactor, combined with the contents therein. The bioreactor may be connected to a mass-measurement device (which may be, e.g., a scale or the like) to continuously or periodically monitor the mass inside the bioreactor (which can be calculated by subtracting the combined mass of the bioreactor with its contents, minus the known mass of the empty bioreactor). In some embodiments, tracking the bioreactor mass is used to monitor flow rates of solutions and samples into and out of (respectively) the bioreactor. In some embodiments, this information is used to ensure a desired combined biomass and solution volume inside the bioreactor.

In some embodiments, readings from pH, dissolved oxygen, temperature sensors in the bioreactor are transmitted to a processor. Based on this information, the processor may control additions of acidic or basic additives, oxygen, and/or carbon dioxide; heating, and stirring, to maintain cell health in the culture. These additions may be driven using pressurized air-driven flow, as described.

In some embodiments, the peripheral compartment of the upstream apparatus (which may be the described "slow" addition module/first peripheral compartment) contains tanks holding liquid supplies to be added to the bioreactor, in a manner that maintains the sterility of the steam sterilized central compartment.

In some embodiments, an additional peripheral compartment or module (which may be referred to as a "fast addition" module or "additional peripheral compartment") constitutes a mechanism for attaching smaller modules in order to make relatively quick and small volume additions to the bioreactor. In some embodiments, the fast module is configured to allow small modules to be attached and removed more quickly than the slow module. In some embodiments, the additional peripheral compartment is configured to be steam sterilized and water cooled, for example as described herein, to speed up the connection process. The second additional/peripheral compartment may contain reagents or components that are relatively labile.

In some embodiments, the additional peripheral compartment(s) include cooling channels that surround the steam chambers. The cooling channels may be between 0.5-3 millimeters, between 0.5-2 millimeters, between 0.5-1.5 millimeters, between 0.8-3 millimeters, between 0.8-2 millimeters, or between 0.8-1.5 millimeters in diameter (measured from the outer walls of the steam chamber outward). In some embodiments, the cooling channels may be in the configuration of a water jacket. In some embodiments, the cooling channels are configured to actively pump water though them, thus enabling rapid cooling of a peripheral compartment after steam sterilization.

In some embodiments, a described method also includes an additional step of moving some or all of the contents of the bioreactor chamber to a downstream container via exertion of differential pressure on the bioreactor chamber. The sample may be conveyed via a product sampling line, which may connect or lead from the bioreactor chamber to the downstream container. In some embodiments, the downstream container is operably connected to a negative pressure line (e.g., separate from the product sampling line and connected via a separate aperture from the product sample line) which transmits negative pressure to the bioreactor chamber. In other embodiments, a positive pressure line connected to the bioreactor (e.g., via compressed air) is utilized.

In some embodiments, the downstream container may be in the aforementioned downstream apparatus. The downstream container may be a container configured to be connected to a second compartment of the downstream apparatus. In some embodiments, direct transport of the product to a container within the first/central compartment, or a similarly equipped compartment, enables seamless transition to downstream processing of the product.

The described upstream apparatus steps may be preceded by the following prior steps pre-a1 and pre-a2, which may be performed in either order or simultaneously: Step pre-A1: sterilely connecting the first and second outgoing pressure lines to the first and second incoming pressure lines (e.g., respectively); and Step pre-A2: sterilely connecting the first and second outgoing fluid lines to the first and second incoming fluid lines (e.g., respectively). In some embodiments, steps pre-A1 and pre-A2 are performed robotically. In some embodiments, steps pre-A1 and pre-A2 may involve a reversible connection.

Use of terminology such as "first and second outgoing pressure lines" is equivalent to referring to the first outgoing pressure line and the second outgoing pressure line, as appropriate for each such instance.

Any of the described upstream or downstream methods may include the additional step of programming a processor to execute a predetermined, choreographed fluid transfer program, e.g., via instructing the actuator(s) to move predetermined amounts of selected fluids at predetermined time intervals. Alternatively or in addition, the processor instructs the actuator(s) to execute fluid transfers based on predetermined milestones. For the upstream apparatus, such milestones may include a desired cell density, viral particle density, or metabolic indicator. The system may be configured to automatically detect these milestones and determine the timing of each process stage accordingly.

In some embodiments, the described downstream apparatus may include an apparatus for joining 2 closed systems. In some embodiments, the downstream methods may utilize a method step for joining closed systems. In some embodiments, the described upstream apparatus may include an apparatus for joining 2 closed systems. In some embodiments, the upstream methods may utilize a method step for joining closed systems.

The systems may be sterilized systems that are joined in a sterile fashion. In some embodiments, the two systems each have an interface, including conduits with fluidly connectable ends. In some embodiments, the ends have a plug and socket configuration (see Figures). The interfaces may have complementary/mirror image geometry, such that multiple conduit ends, if present, can mate with one another the conduits may be surrounded by walls configured to form an airtight, sterilizable or steamable chamber enclosure when the interfaces are juxtaposed to one another. A gasket may be present to assist in the formation of airtight chamber(s). The interfaces may be rigidly and reversibly connected to one another.

In some embodiments, the joining and/or sterilization process includes some or all of the following steps: In the first step (disconnected mode), the two components of the chamber enclosure are disconnected. In the second step (chamber connected mode) the two chamber enclosure components are rigidly juxtaposed, thereby forming an airtight chamber seal. In some embodiments, this is accomplished by an impetus resulting from activation of a linear (force) actuator, e.g., a component configured to transmit a linear force. The two conduit ends remain detached in this step. In the third step (sterilization), steam or another sterilizing gas is brought into the chamber. In some embodiments, this is accomplished via steam routing channels, which may be disposed in a manifold block (see FIG. 18). This sterilizes the chamber(s). In the fourth step (fluidic connected mode), the two conduit ends are juxtaposed. In some embodiments, this is caused by further action of the actuator. In some embodiments, when multiple connectors are present, each connection is formed individually. In other embodiments, multiple connections are formed simultaneously. In some embodiments, after the steam sterilization step, the ends are maintained in a sterile environment until after the fluid connection is consummated. In some embodiments, a sterile environment is maintained until the conduit ends are disconnected. A sterile environment refers to an environment that has been sterilized and is kept within an airtight enclosure.

Structural features of the described systems may be freely combined with process steps of the described methods. The described structural features are hereby incorporated into the described methods. The described method steps are hereby incorporated into the described systems.

Apparatuses and methods described herein are illustrative. Apparatuses and methods in accordance with this disclosure will now be described in connection with the figures, which form a part hereof. The figures show illustrative features of apparatus and method steps in accordance with the principles of this disclosure. It is to be understood that other embodiments may be utilized and that structural, functional and procedural modifications may be made without departing from the scope and spirit of the present disclosure.

The steps of methods may be performed in an order other than the order shown or described herein. Embodiments may omit steps shown or described in connection with illustrative methods. Embodiments may include steps that are neither shown nor described in connection with illustrative methods.

Illustrative method steps may be combined. For example, an illustrative method may include steps shown in connection with another illustrative method.

Apparatuses may omit features shown or described in connection with illustrative apparatuses. Embodiments may include features that are neither shown nor described in connection with the illustrative apparatus. Features of illustrative apparatus may be combined. For example, an illustrative embodiment may include features shown in connection with another illustrative embodiment.

FIG. 1 depicts a schema of a system 100 for biochemical purification, in accordance with principles of the disclosure. System 100 may include a first compartment 150 and a second compartment 160, which are reversibly connectable to one another (indicated by double-headed arrows) at interface 128. Pressure actuator 102 is configured to transmit pressure via gas conduit 104 to first sample container 106, causing sample (indicated by gray shading) to move via first sample conduit 108 to first connector 140, which connects to fifth connector 144, which connects to upstream end 117 of fractionation moiety 116, which is located within second compartment 160. Connection between fifth connector 144 and fractionation moiety 116 may be either direct or via optional first additional sample line 114. Pressure from actuator 102 may move sample from upstream end 117 into downstream end 119 of fractionation moiety 116. Fractionation moiety 116 may optionally include filter 118. Pressure from actuator 102 may move sample from downstream end 119 to sixth connector 145, which connects to second connector 141, which connects to second sample conduit 122, which connects to second sample container 124. Connection between fractionation moiety 116 and sixth connector 145 may be either direct or via optional second additional sample line 120. Second compartment 160 also contains reagent container 126, which connects to eighth connector 147, which connects to fourth connector 143, which connects to reagent conduit 130, third connector 142, seventh connector 146, and fractionation moiety 116. Connection between reagent container 126 and eighth connector 147 may be either direct or via optional first additional reagent line 133. Connection between seventh connector 146 and fractionation moiety 116 may be either direct or via optional second additional reagent line 132.

With further reference to FIG. 1, connectors 140-143 are located within orifices within interface side 110 of first compartment 150. Connectors are depicted as circles, and orifices as unnumbered squares. Connectors 144-147 are located within connector manifold 112 of second compartment 160.

Figure 2A:
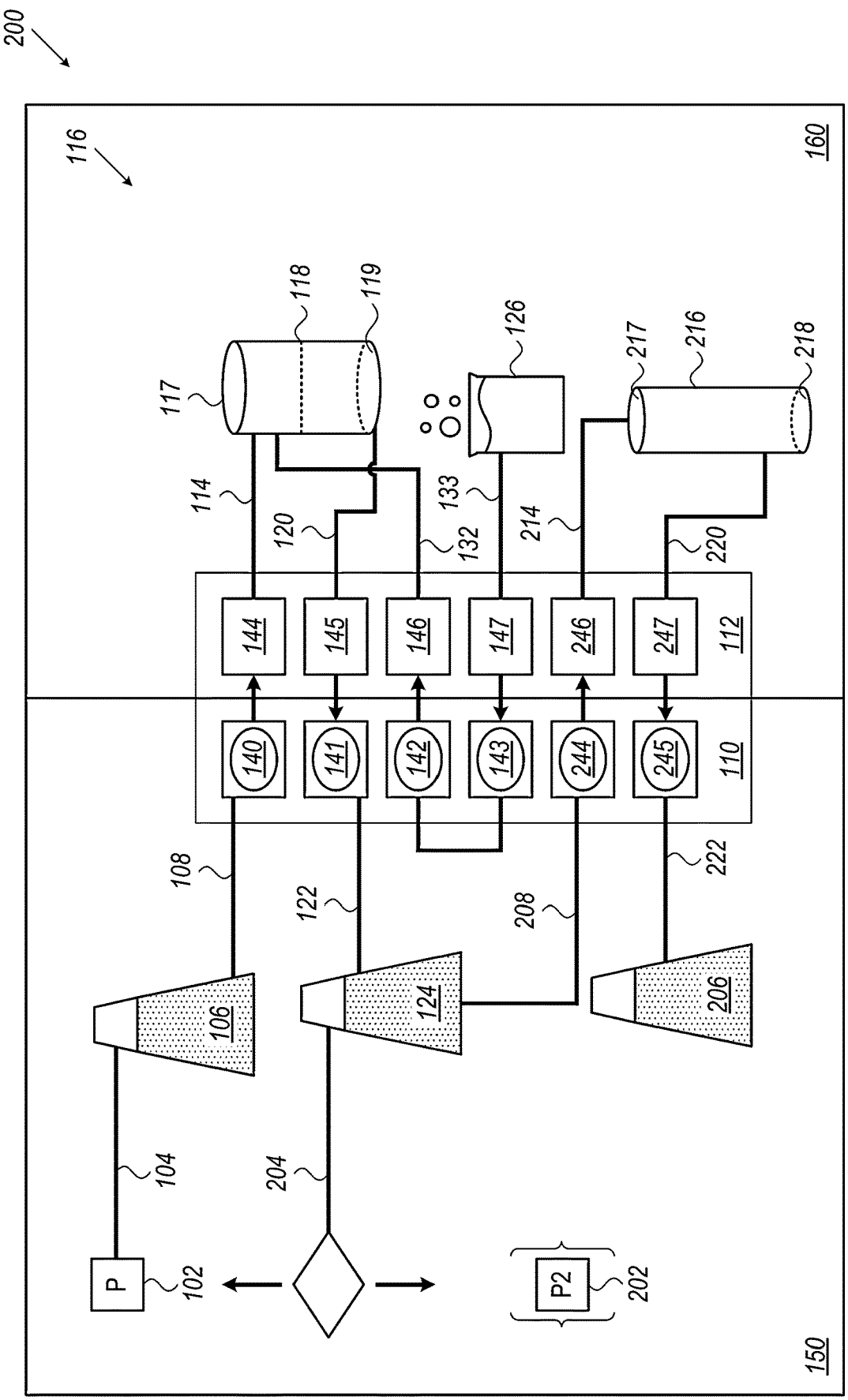
FIG. 2A depicts a schema of a system for biochemical purification.
Figure 2B:
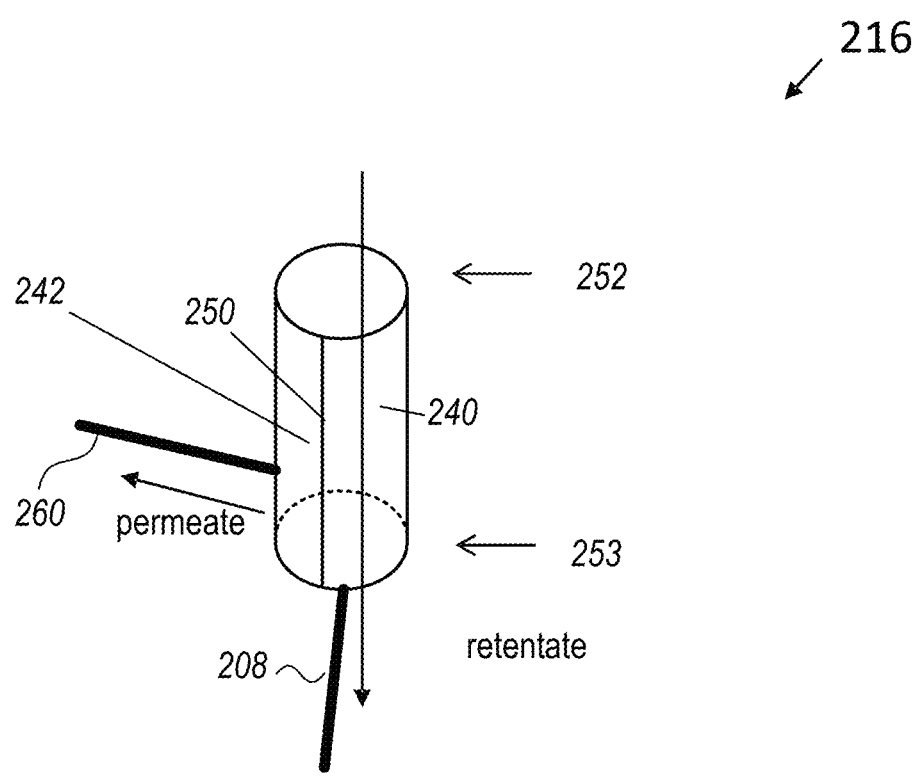
FIG. 2B depicts a view of a tangential flow filtration apparatus.

FIG. 2A depicts a schema of a system 200 for biochemical purification, in accordance with principles of the disclosure.

In addition to the components described for FIG. 1, system 200 includes connectors 244-247, third sample container 206, optional second pressure actuator 202, second gas conduit 204, third sample conduit 208 and fourth sample conduit 222, and second fractionation moiety 216.

With further reference to FIG. 2A, depending on the configuration, either pressure actuator 102 or 202 is configured to transmit pressure via second gas conduit 204 to second sample container 124, causing sample (indicated by gray shading) to move via third sample conduit 208 to ninth connector 244, which connects to eleventh connector 246, which connects to upstream end 217 of second fractionation moiety 216, which is located within second compartment 160. Connection between eleventh connector 246 and second fractionation moiety 216 may be either direct or via optional third additional sample line 214.

With further reference to FIG. 2A, pressure from second gas conduit 204 may move sample from upstream end 217 into downstream end 218 of second fractionation moiety 216. Pressure from second gas conduit 204 may move sample from downstream end 218 to twelfth connector 247, which connects to second connector 244, which connects to fourth sample conduit 222, which connects to third sample container 206. Connection between second fractionation moiety 216 and twelfth connector 247 may be either direct or via optional fourth additional sample line 220.

Figure 12:
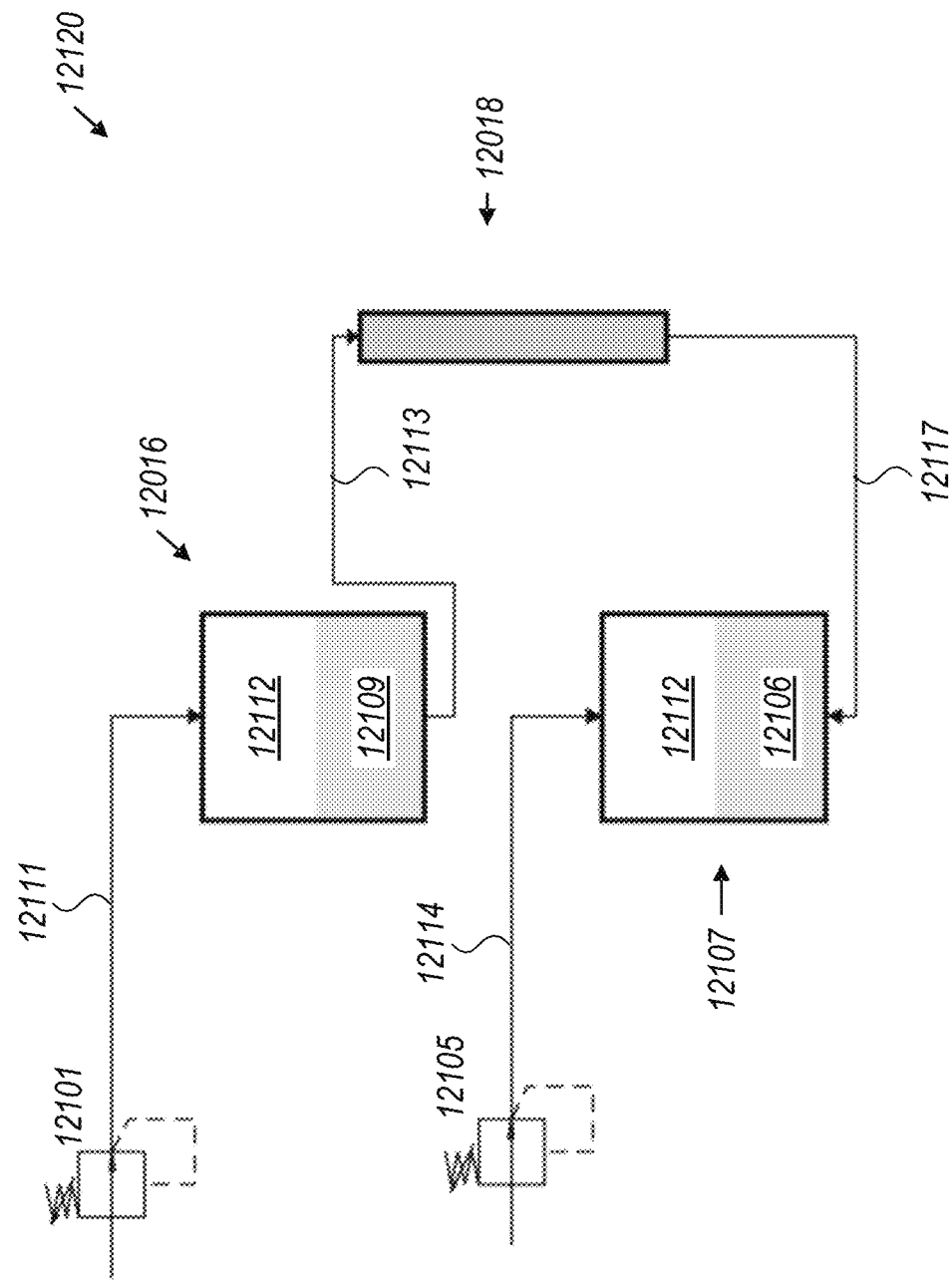
FIG. 12 is a schematic depiction of a described fluid propulsion system.

FIG. 2B is a magnified view of an exemplary TFF apparatus 256, in accordance with principles of the disclosure. TFF apparatus 256 is one possible embodiment of the second fractionation moiety 216 of FIG. 2A, and this embodiment may be used generally as a fractionation moiety in the described methods and systems. In TFF apparatus 256, sample flows from upstream end 252 to downstream end 253, as indicated by the arrow. Alternating, bidirectional flow may optionally be used, for example as shown in FIG. 12. Flow is parallel to filter 250. Sample flows through first region 240 in the direction of the arrow. Pressure in first region 240 may force molecules smaller than the filter pores into second region 242. The filtrate, containing these molecules, may exit second region 242 via waste conduit 260. The retentate, containing the sample, may exit first region 240 via third sample conduit 208.

Figure 3:
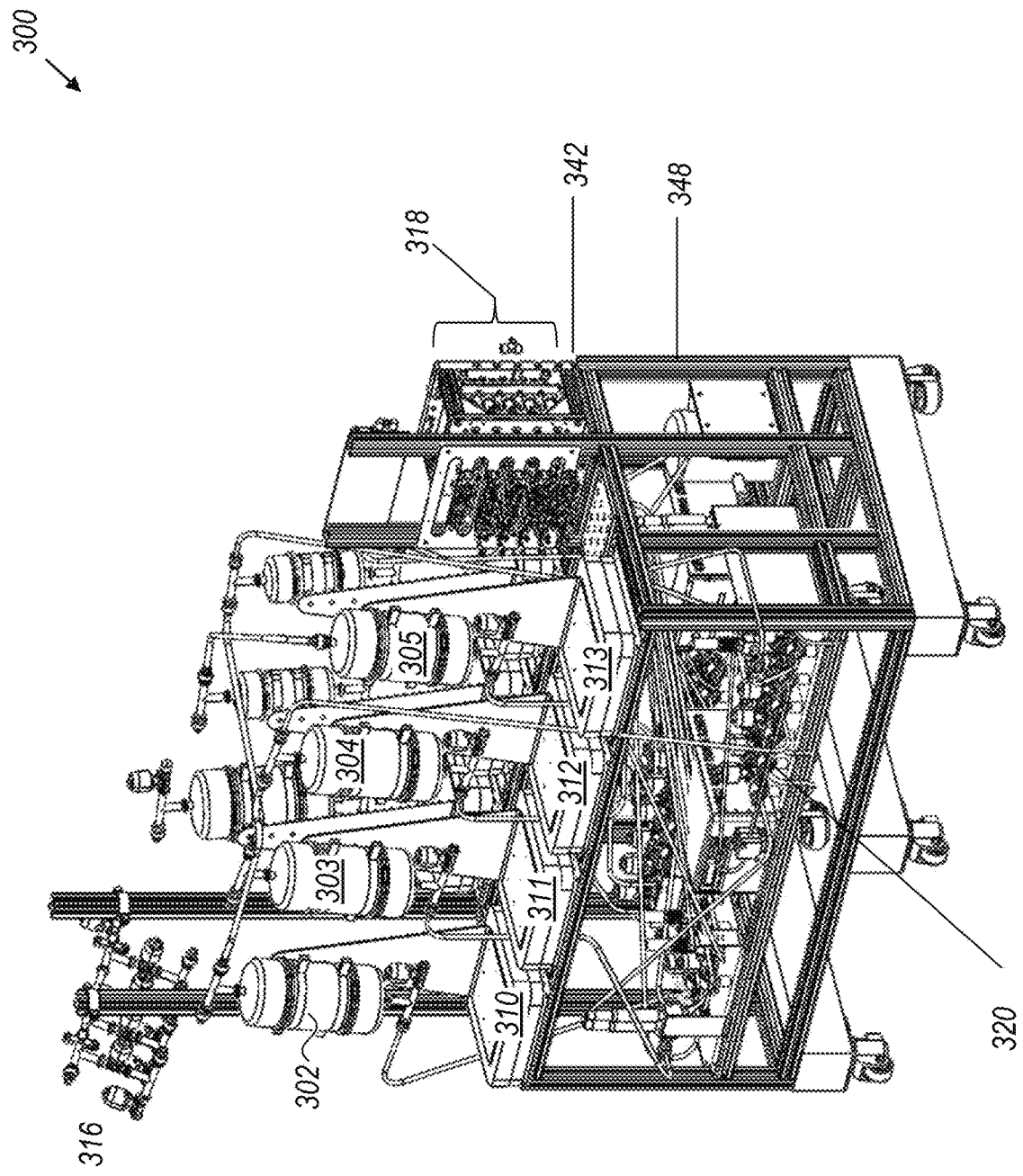
FIG. 3 depicts an oblique view of a compartment of a biochemical purification apparatus.

FIG. 3 shows an oblique view of first compartment 300 of a biochemical purification (also referred to as "downstream") apparatus, in accordance with principles of the disclosure. Seven tanks are present, with 4 tanks, numbered 302-305, fully visible in this view. Tanks 302-305 are suspended on L-shaped mounting plates (see FIG. 4), which rest on scales 310-313, respectively. As fluid is added or samples are removed from a tank, its mass will change, from which the flow rate and mass transfer can be deduced. Also shown are utility distribution manifold 316, which can be used to route pressurized air, steam, and cleaning fluid, and fluid diversion/outlet valve manifold 320. FIG. 3 provides an oblique view of the side of connection interface 318. Scales 310-313, connection interface 318, and associated apparatus are attached to and supported by rigid baseplate 342. Depicted components are attached to and organized and supported by rigid frame 348. Connection interface 318 serves to connect first component to second component (not shown).

Figure 4:
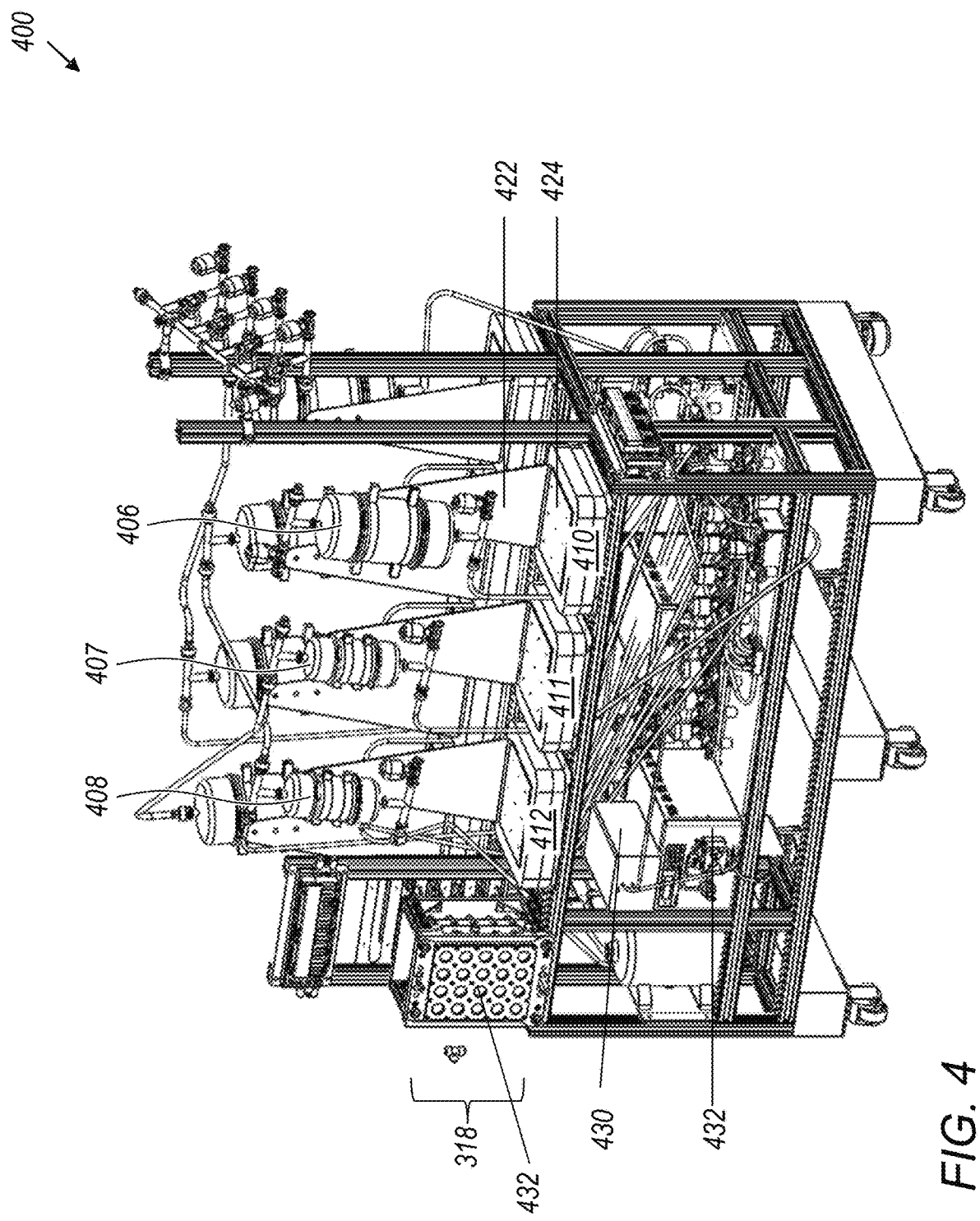
FIG. 4 depicts an oblique view of a compartment of a biochemical purification apparatus.

FIG. 4 shows an oblique view of first compartment 400 of a biochemical purification apparatus, in accordance with principles of the disclosure. View is rotated nearly 180 degrees in a horizontal plane, relative to FIG. 3, providing an unobscured view of the remaining 3 tanks, 406-408. This view also provides an oblique, nearly frontal view of steam manifold block 432 on connection interface 318. Tanks 406-408 are suspended on L-shaped mounting plates 422, with the bottom section 424 of each mounting plate resting on one of scales 410-412, respectively. Inline degasser 430 and pulseless constant flow pump 432 are also depicted.

Figure 5:
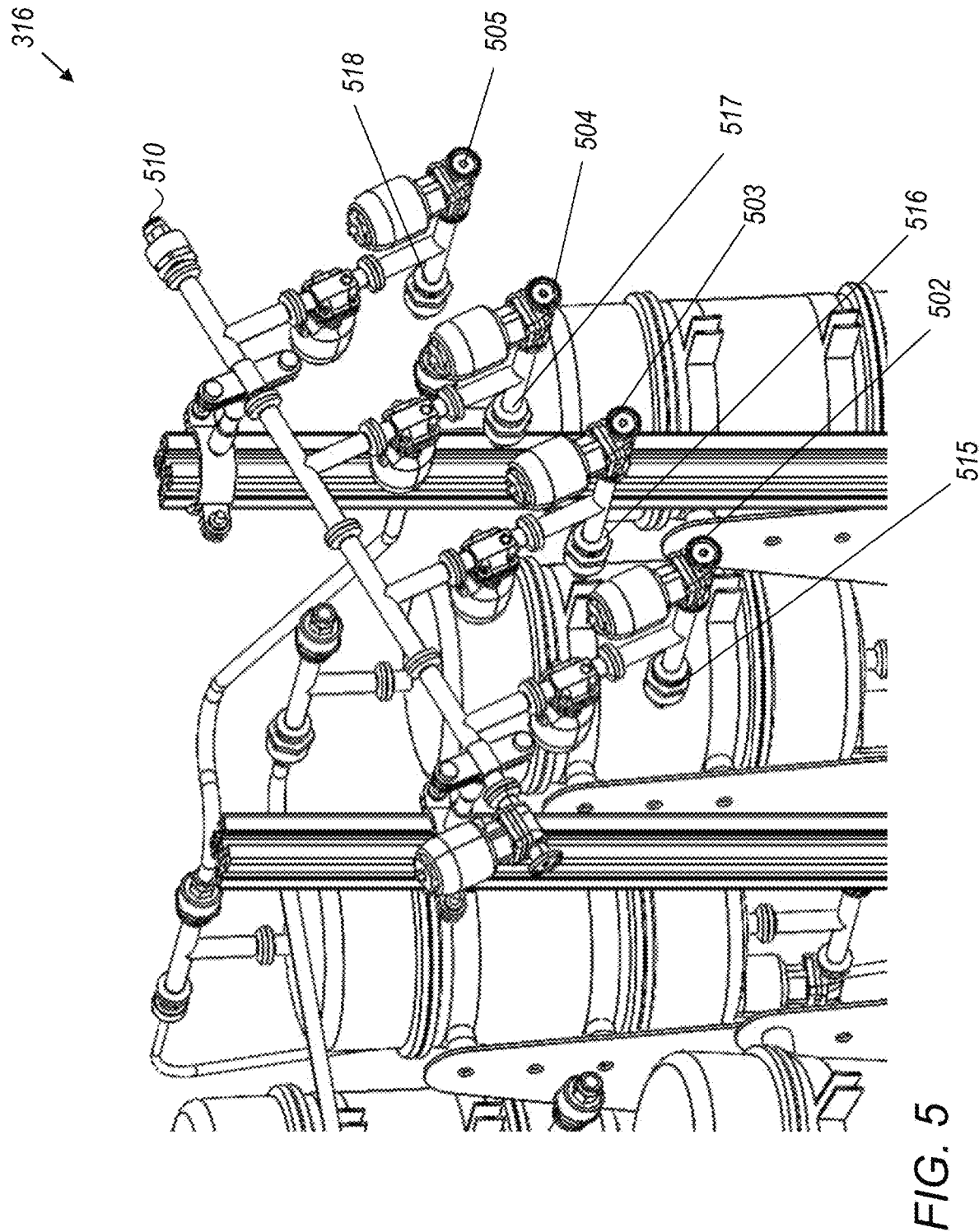
FIG. 5 depicts a magnified view of utility distribution manifold.

FIG. 5 shows a magnified view of utility distribution manifold 316, in accordance with principles of the disclosure. FIG. 5 shows four individually controllable air lines 502-505, steam/cleaning fluid main line inlet 510, and outlets 515-518, leading to headspaces of the tanks.

Figure 6:
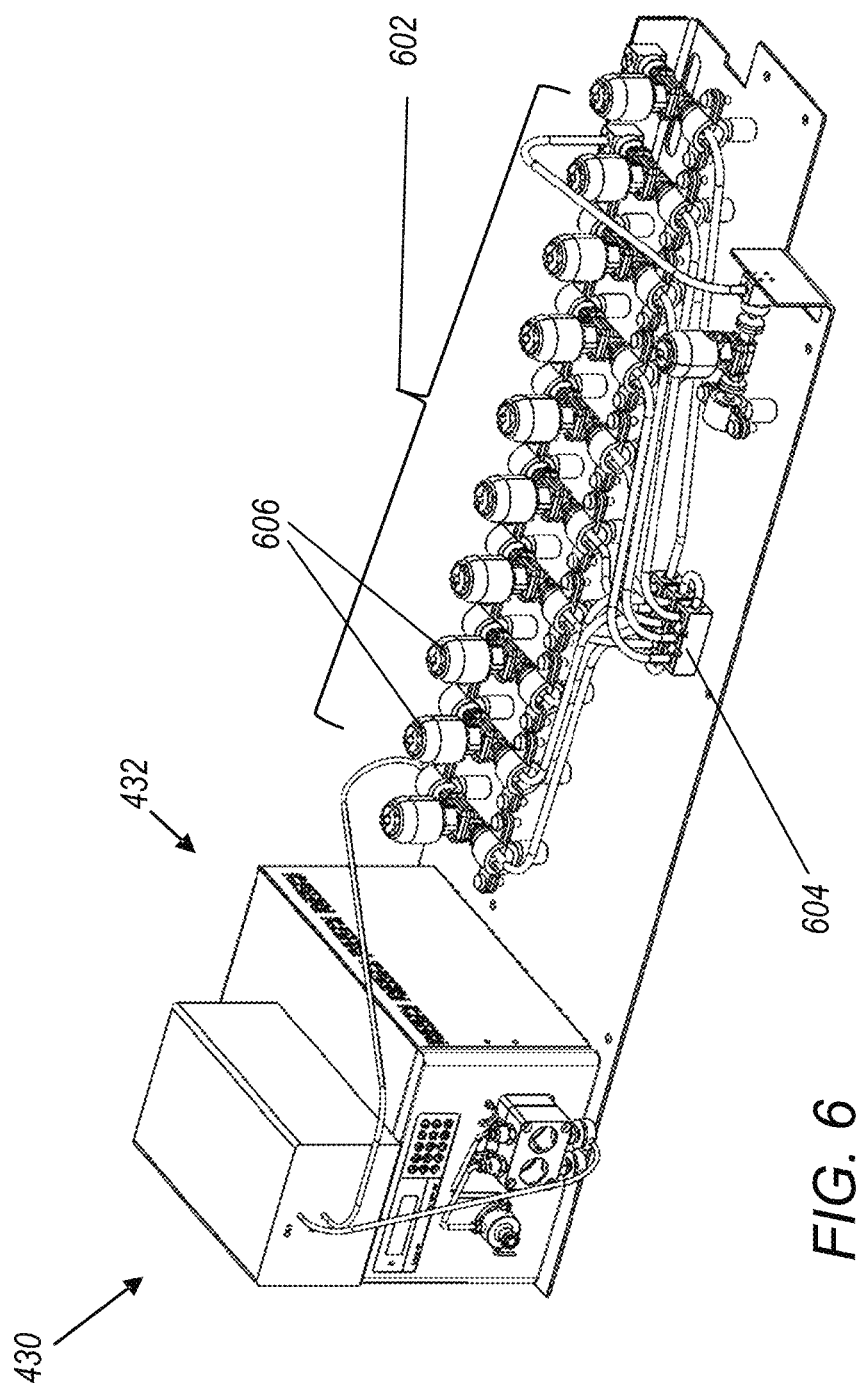
FIG. 6 depicts a magnified view of fluid diversion manifold, constant rate flow pump, and inline degasser.

FIG. 6 shows a magnified view 600 of constant rate flow pump 432, and inline degasser 430, in accordance with principles of the disclosure. Valve array 602 connects to tanks and/or sterile interface. Depicted are crevice-free manifold array 604 and reagent inlet valves 606 of the manifold.

Figure 7:
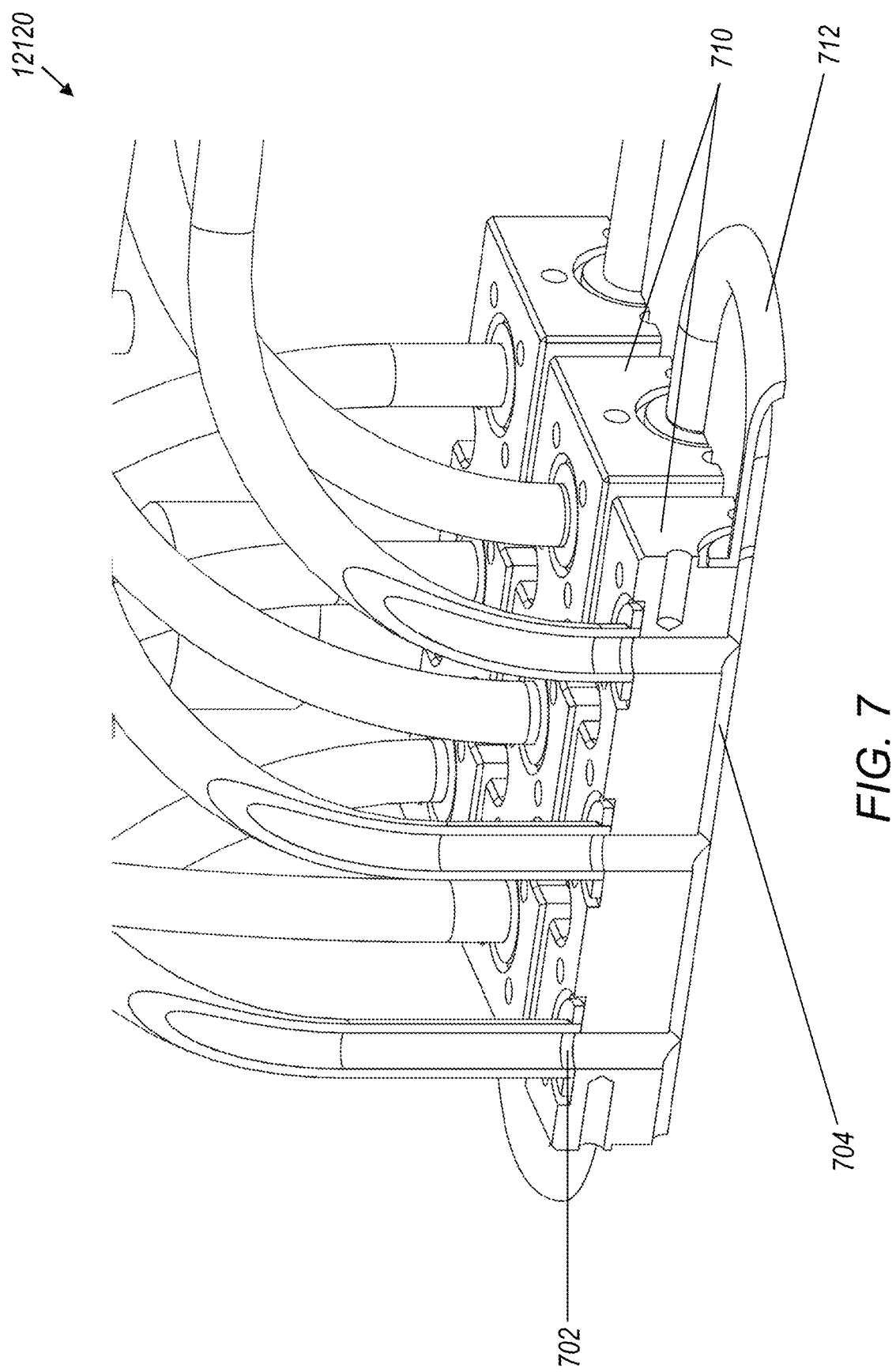
FIG. 7 depicts a magnified, cutaway view of a crevice-free manifold array.

FIG. 7 shows a further magnified, cutaway view of crevice-free manifold array 604, in accordance with principles of the disclosure. Shown are individual manifolds 710, the location of tube flange termination 702, a smooth, cross drilled bore 704 in the main manifold flow channel, and a jumper 712, which links the individual manifolds.

Figure 8:
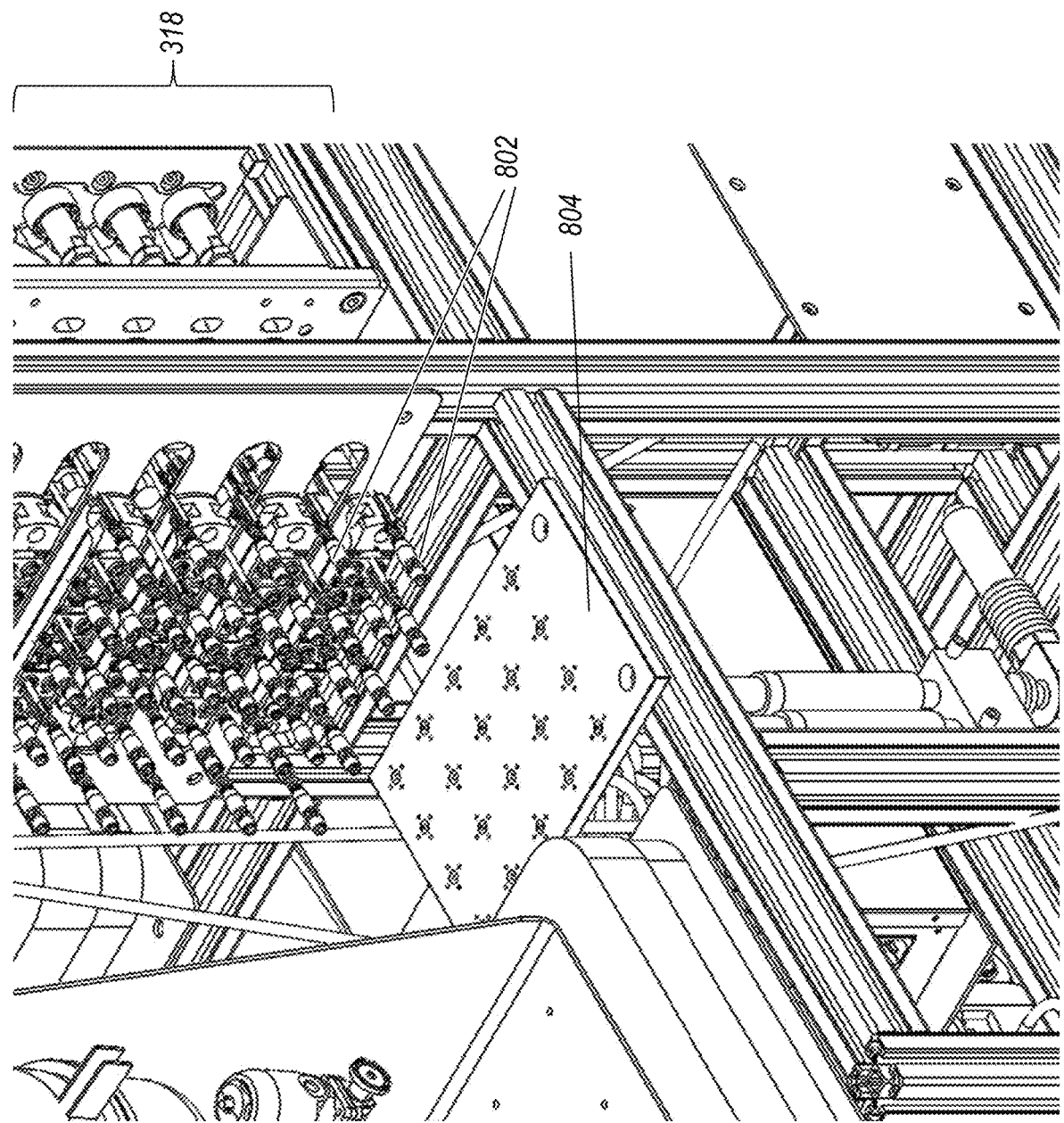
FIG. 8 depicts a magnified view of an adaptor plate and actuator limit switches of a connection interface.

FIG. 8 shows a magnified view 800 of adaptor plate 804 and actuator limit switches 802 of connection interface 318, in accordance with principles of the disclosure.

Figure 9:
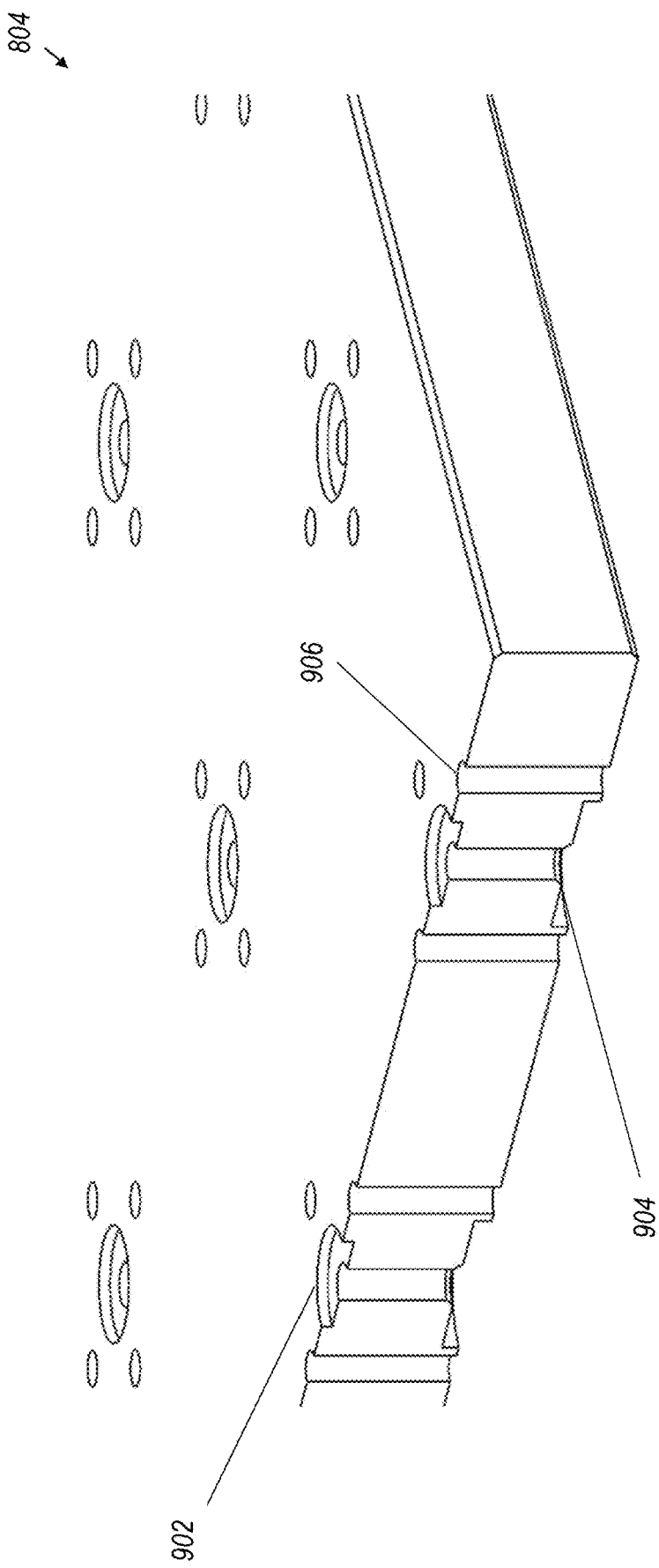
FIG. 9 depicts a further magnified view of an adaptor plate.

FIG. 9 shows a further magnified, cross section of a tube sizing adapter plate 804, in accordance with principles of the disclosure. Adapter plate 804 enables a transition between flanged tubes having different sized bores. Locating feature 902 for a flanged tube, bore size transition region 904, and retaining feature for flanged tube 906 are indicated.

Figure 10:
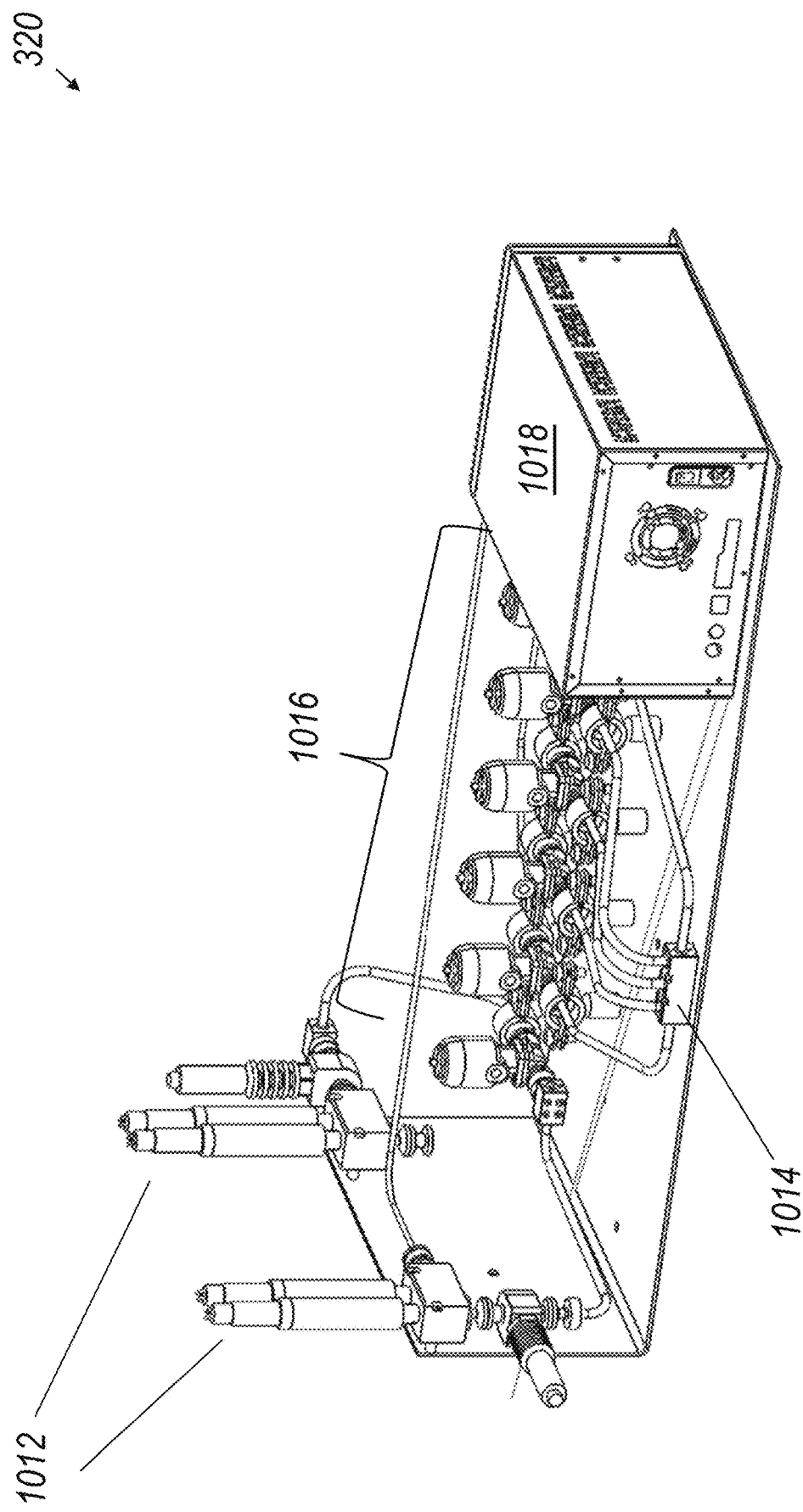
FIG. 10 depicts a fluid diversion/outlet valve manifold.

FIG. 10 shows a fluid diversion/outlet valve manifold 320, which may be configured to divert module output to the appropriate tank/flow path for next unit operation. Also visible are the pre- and post-module sensing stacks 1012 for pH, conductivity, and pressure; crevice free manifold 1014; valve array 1016; and UV sensor 1018.

Figure 11:
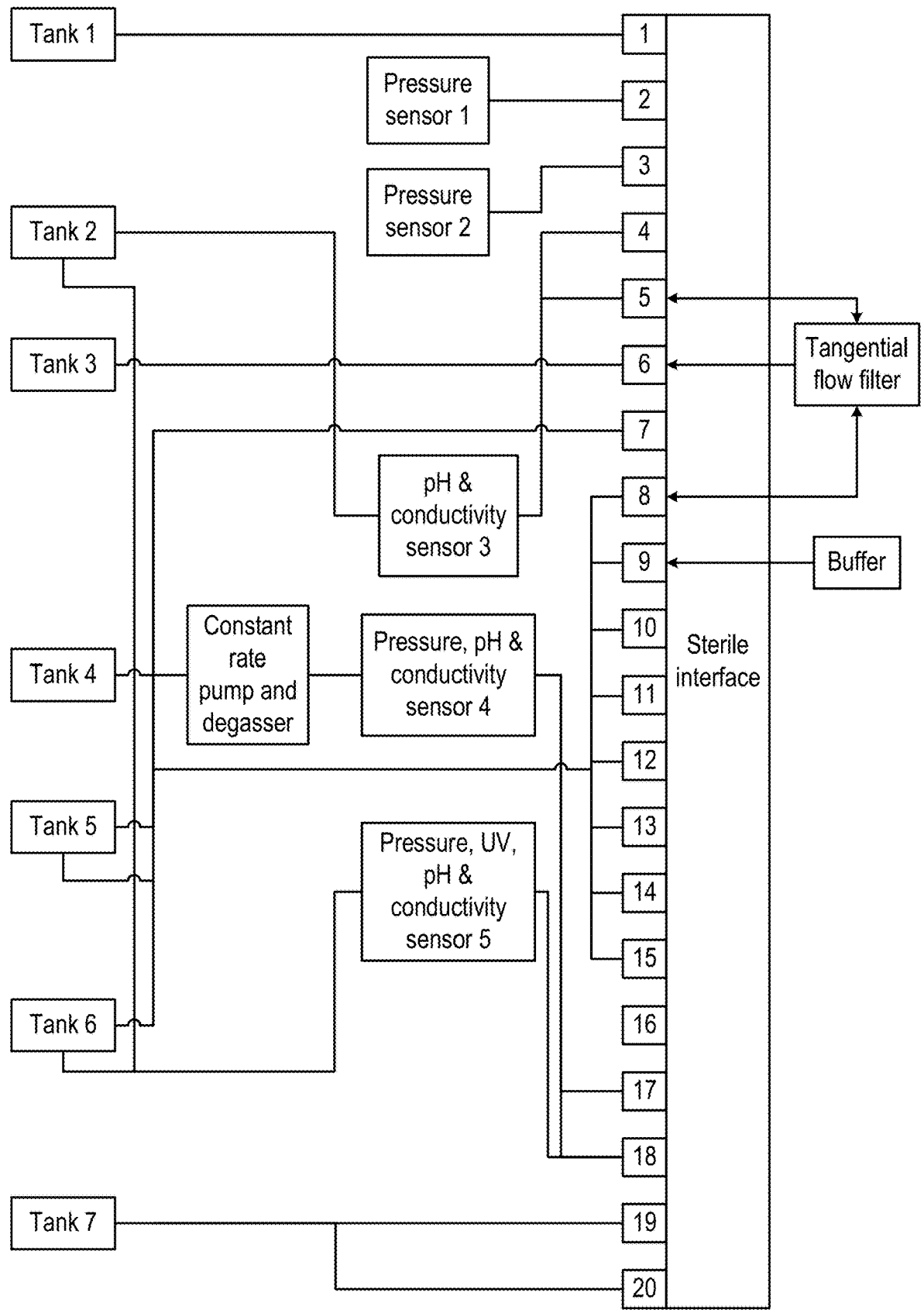
FIG. 11 a possible component arrangement of a system.

Solely for exemplification, FIG. 11 shows a possible arrangement of sample tanks; conduits; pressure, pH, and conductivity sensors; and a pump, all connected to a TFF apparatus and TFF buffer tank, via an interface.

FIG. 12 is a schematic depiction of a system 12120, in accordance with principles of the disclosure, for bidirectionally impelling a sample out of tanks and across a separation moiety 12018, in accordance with principles of the disclosure. First pressure actuator 12101, which may be a pressure regulator, may be programmatically set to a predetermined pressure level by a controller (not depicted). If the mentioned pressure level is greater than the pressure in the proximal air line 12111, which is disposed downstream relative to first actuator 12101, then pressured air flows through the proximal air line. Pressurized air proceeds through air line 12111 to headspace 12112 of first sample container 12016. Increased pressure in headspace 12112 impels sample 12109 out of container 12016, through downstream fluid line 12113, into separation moiety 12018.

To reverse flow of fluid through separation moiety 12018, second pressure actuator 12105, which may be a pressure regulator, is set to a pressure level by a controller. First pressure actuator may be switched to passive (venting) mode or set to a lower pressure than second pressure actuator. Pressurized air is impelled through second proximal air line 12114, into headspace 12112 of second sample container 12107, impelling sample 12106 through second downstream fluid line 12117 into separation moiety 12018.

Alternating, two-way movement of fluid back and forth through separation moiety 12018 may be performed by alternating higher pressures between pressure actuators 12101 and 12105.

Figure 13:
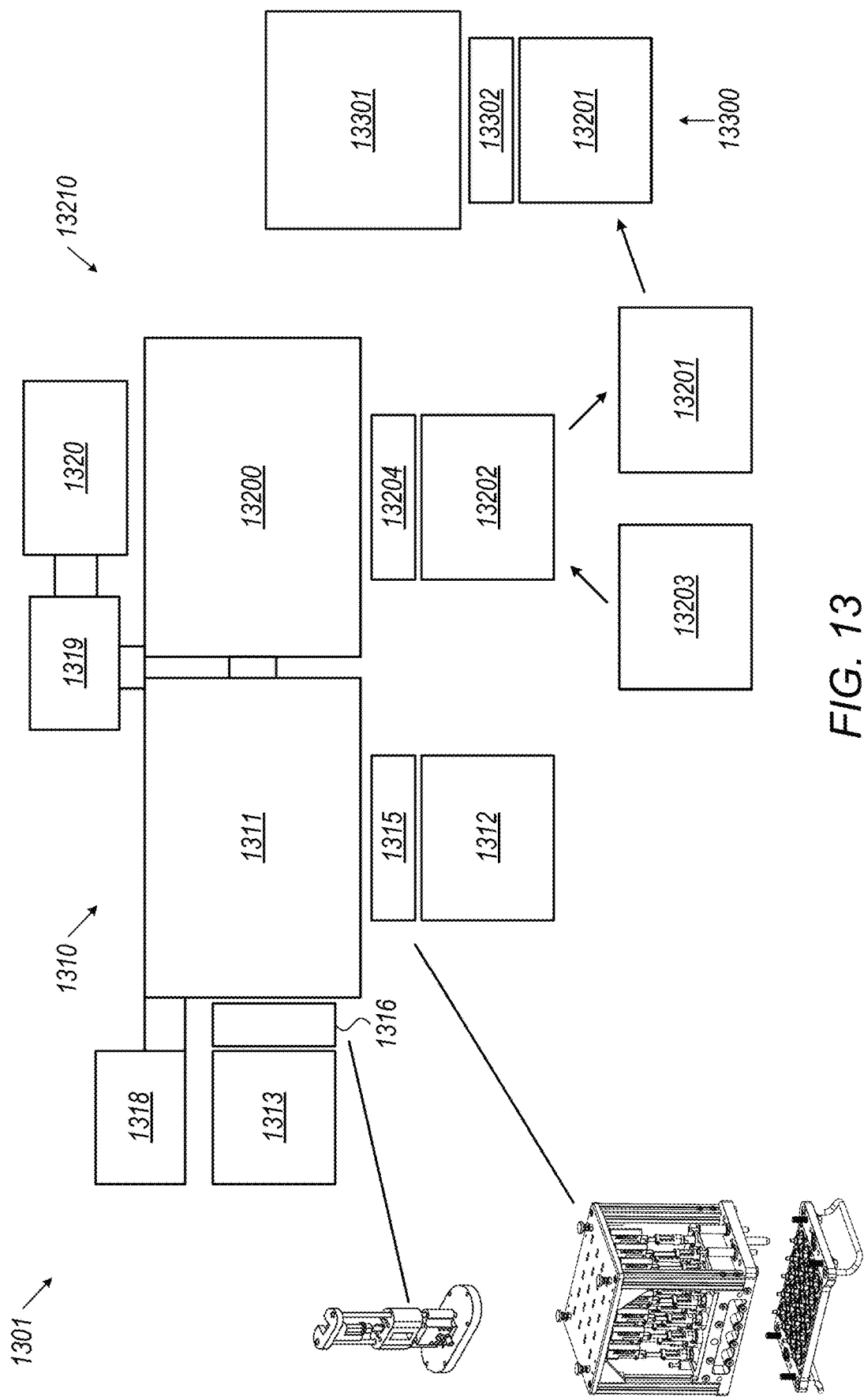
FIG. 13 is a schematic system architecture overview.

FIG. 13 is a schematic system architecture overview of system 1301, in accordance with principles of the disclosure. System 1301 includes upstream apparatus 1310 and downstream apparatus 13210. Upstream apparatus includes central (sub) compartment 1311, which may be fixed in place and contains bioreactor chamber (not depicted). First apparatus connects to "slow" upstream module 1312 (also referred to as "peripheral compartment") and "fast" upstream module 1313 (also referred to as "additional peripheral compartment"), containing fluid containers (not depicted), via slow module interface 1315 and fast module interface 1316, respectively. Central compartment 1311 also may connect to utility lines 1318 (depicted schematically by box), such as gas, steam, and cleaning fluid (not depicted). Upstream apparatus 1310 and/or downstream apparatus 13210 may be connected to power/data lines 1319, which in turn may connect to supervisory control and data acquisition system 1320.

With further reference to FIG. 13, first compartment 13200 of downstream apparatus 13210 may connect sequentially to second compartments 13201-13203 via downstream interface 13204, which may be identical in structure to slow module interface 1315. Module handling system 13300, including Reuse (Clean/Sterilize/Fill) Station 13301, can be used to clean any of downstream second compartments 13201-13203 (depicted for downstream second compartment 13201) via cleaning interface 13302.

Figure 14:
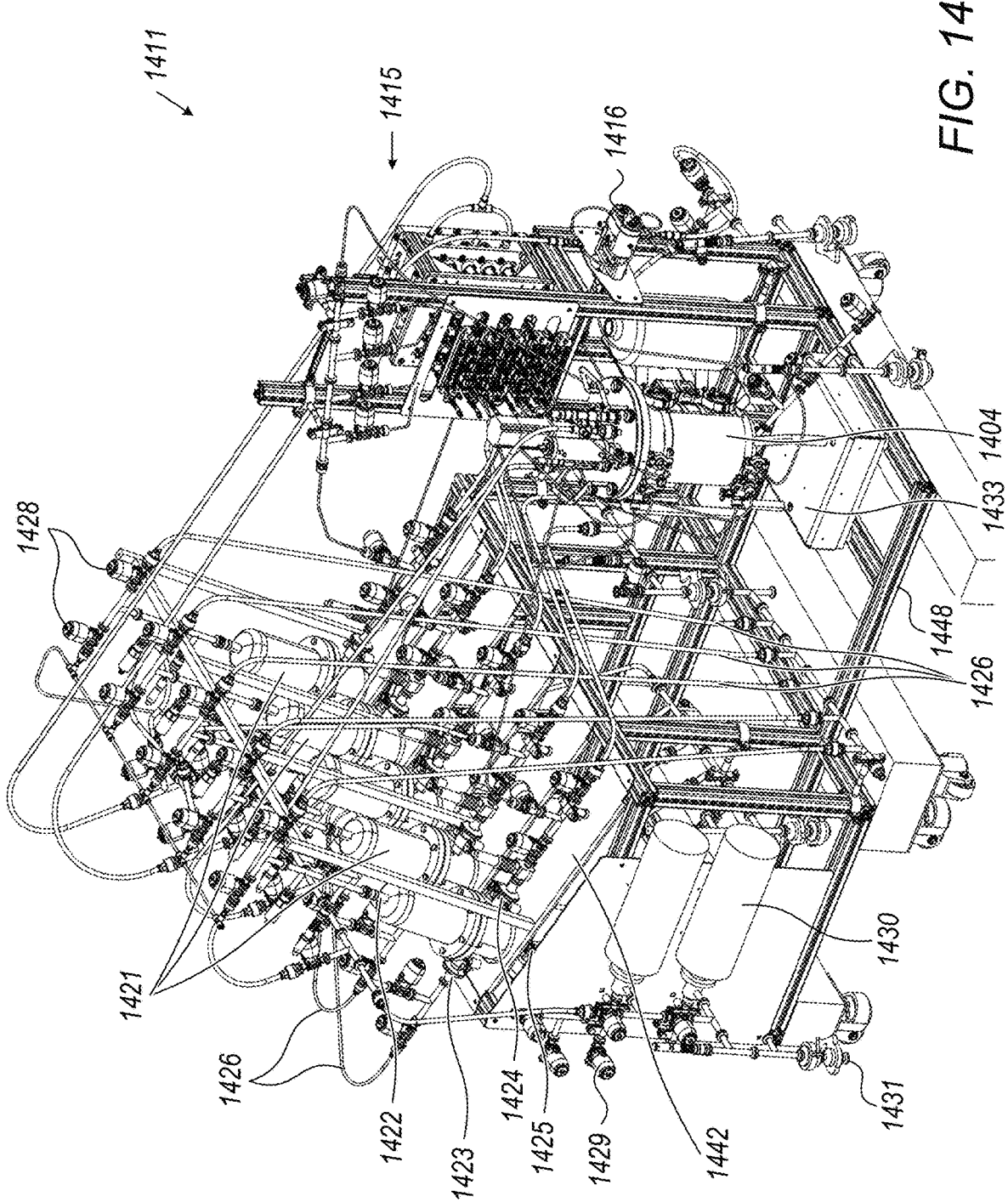
FIG. 14 shows a perspective cutaway view of a central compartment of a described system.

FIG. 14 shows a perspective cutaway view of central compartment 1411 of upstream apparatus, in accordance with principles of the disclosure. Sterile air filters 1421 are connected via air lines 1426, which can carry air to an upstream pressure regulator. This regulator sets and maintains the inlet air pressure to induce air flow through the filter. Temperature and pressure are measured using sensors. Each sterile air filter 1421 has a vent 1422 an inlet 1423, an outlet 1424, and a drain 1425. Valves 1428 are placed at each of these ports to control flow through different paths through or around the filter. The flow path depends on whether an automated sterilization protocol or process protocol is being run. Bioreactor 1404, attachment sites of slow 1415 and fast 1416 modules are also depicted. Sterile air filters 1421 and associated apparatus are attached to and supported by rigid baseplate 1442. Depicted components are attached to and organized and supported by rigid frame 1448.

Filters 1421 are steamed through their inlet 1423, across the filter membrane (not depicted), and out the outlet 1424. The vent 1422 and drain 1425 may be used for pre-heating air filters 1421 and filter integrity testing. The auxiliary utility valves 1429 (which can be used for water, cleaning fluid, and steam) and equipment are used to route steam into the system from optional control valves 1430, and route condensate out of the system through a system of system drains 1431. Pipes may be angled for optimal draining.

The bioreactor 1404 may rest on a scale 1433 to continuously or periodically monitor the mass inside the bioreactor. As fluid is added or samples are removed from the bioreactor, its mass will change, from which the flow rate and mass transfer can be deduced.

The "slow", or fixed addition module (shown in detail in later figures; also referred to as "peripheral compartment") may be a mechanism for connecting modules in a manner that maintains the sterility of the steam sterilized station. The "Fast Addition" or "additional peripheral" module interface 1415 (shown in detail in later figures) may serve to attach smaller modules for quick, small additions to the bioreactor. These module(s) can also be used to take samples. They are a smaller version of the slow module, and they may be intended to allow small modules to be attached and removed more often than the slow module. The Fast Addition module may be steam-sterilized and actively water cooled to speed up the connection/disconnection process. Similar components may be present in first compartment of downstream apparatus.

Figure 15:
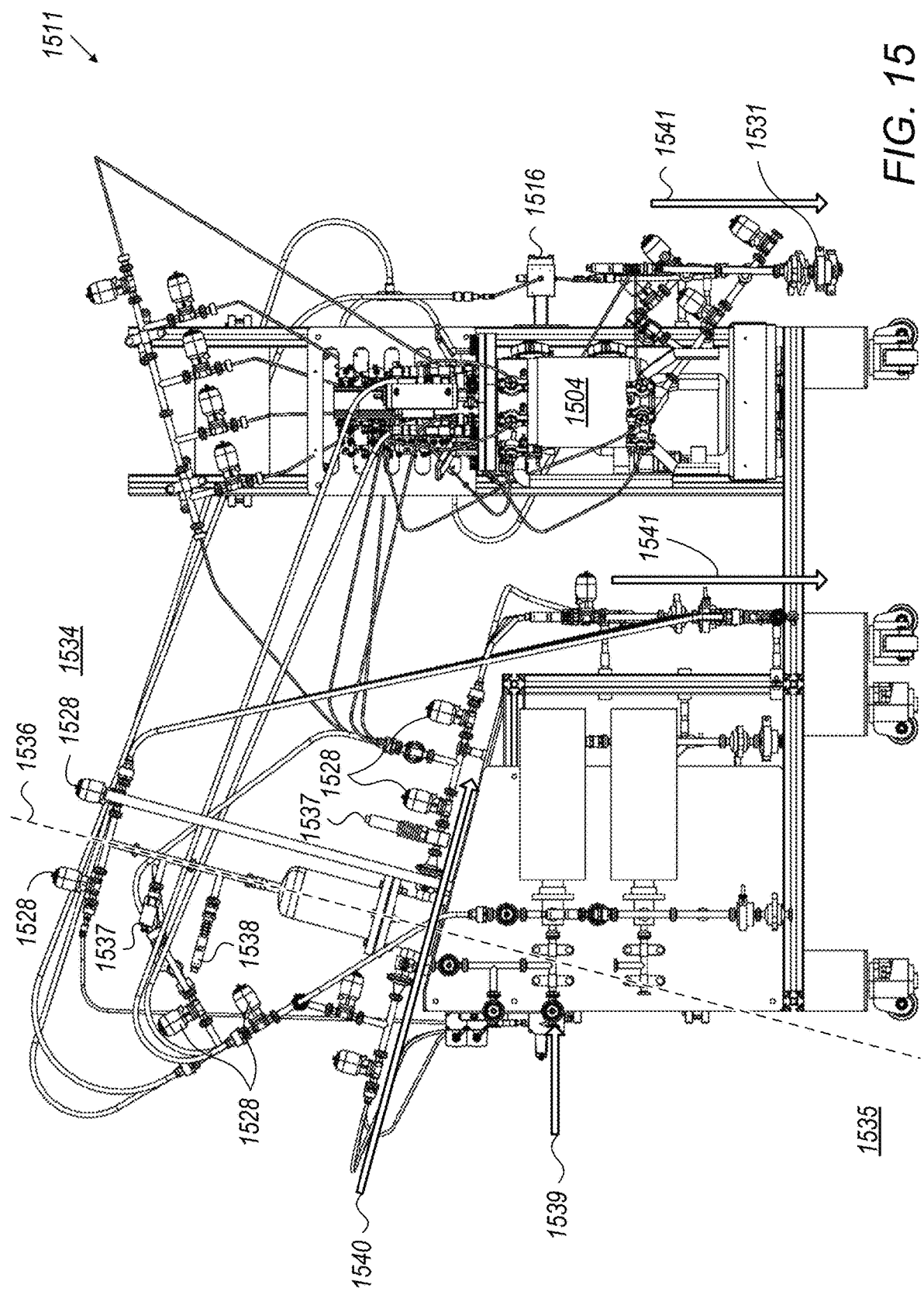
FIG. 15 depicts a side view of a central compartment of a described system.

FIG. 15 depicts a side view of central compartment 1511 of upstream compartment or apparatus, highlighting the separation between sterile air side 1534 and non-sterile air side 1535, created by sterile filter membrane (demarcated by dotted line 1536), in accordance with principles of the disclosure. The sterile filter does not allow microbes to pass through its membrane, maintaining sterility on the sterile air side. The sterile boundary is also maintained across our two interfaces, which are depicted in later figures. Fast addition interface 1516, valves 1528, system drains 1531, pressure 1537 and temperature gauges 1538, and main steam inlet 1539 are also depicted. Diagonal arrow 1540 shows air flow direction. Vertical arrows 1541 show condensation flow direction.

Figure 16:
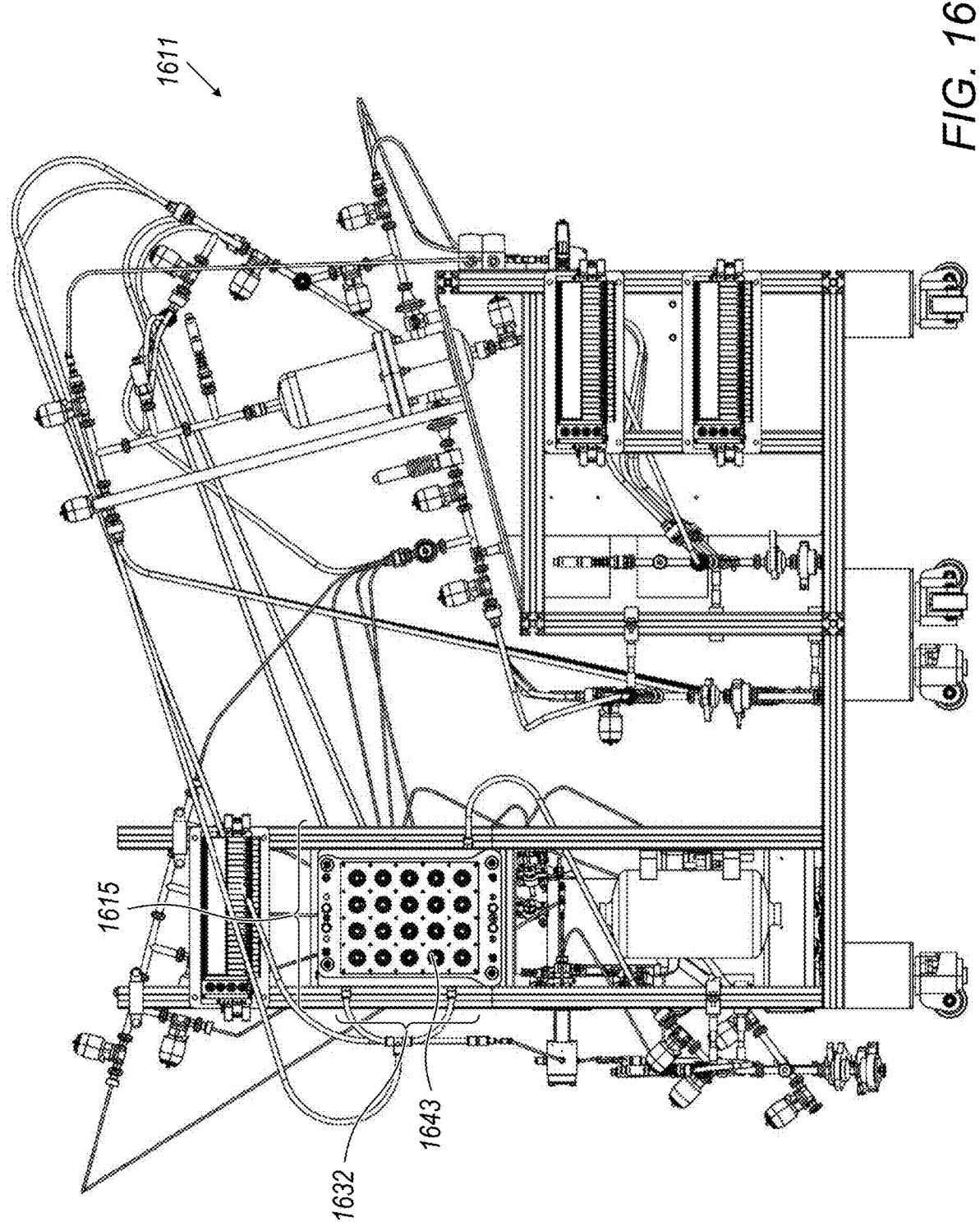
FIG. 16 depicts a side view of a central compartment of a described system, rotated 180 degrees in a horizontal plane relative to the previous figure.

FIG. 16 depicts a side view of central compartment 1611 of upstream compartment or apparatus, rotated 180 degrees in a horizontal plane relative to the previous figure, in accordance with principles of the disclosure. This figure depicts the "Slow" peripheral compartment (also referred to as "module") interface 1615 without a module connected, revealing gasket seal 1632 of the interface 1615, forming an airtight seal for steam sterilizing the connection chambers formed between the central compartment (shown here) and the "Slow" peripheral compartment side (depicted in later figures). Attachment of a (pre-sterilized, closed) module (not depicted) to interface 1615 forms up to 20 sealed chambers (depicted in later figures), one around each fluidic connector pair (depicted in later figures), each pair including central-side connector 1643. The chambers may then be steam sterilized, bringing the pre-sterilized module across the sterile boundary of the pre-sterilized station without contaminating either sterile, closed system.

Figure 17:
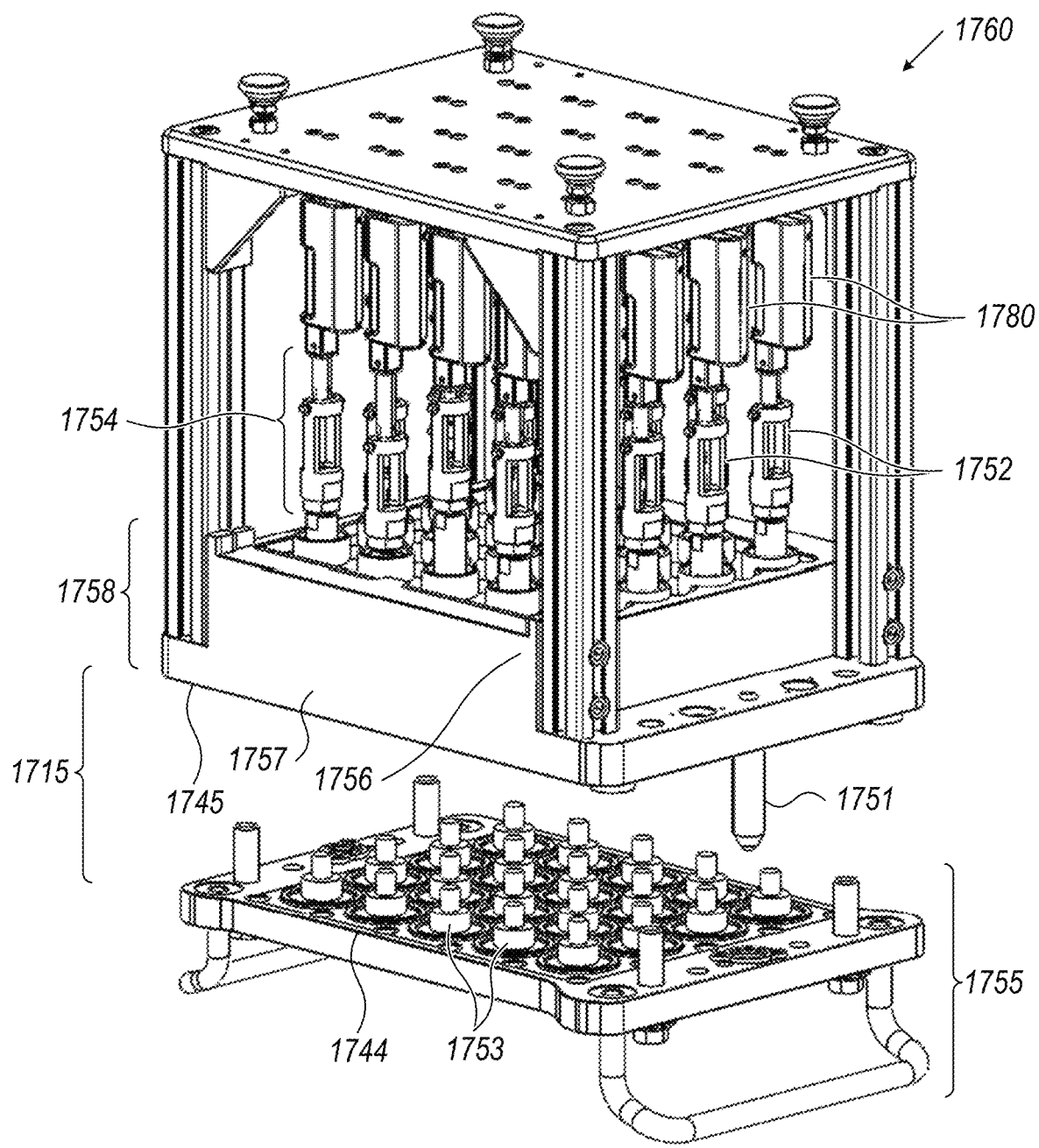
FIG. 17 depicts a perspective, cutaway view of a steamable interface, including arrayed connectors.

FIG. 17 depicts a perspective, cutaway view of a steamable interface including arrayed connectors, showing a possible array arrangement 1754 of central-side connectors 1752 and linear actuators 1780 of central side component 1760 of slow module interface 1715, in accordance with principles of the disclosure. Attachment may be guided by 1-2 alignment pins, one of which, 1751, is visible in this view. Alignment pin 1751 and central-side connector termini (not visible) protrude from interface-side edge 1745 of central side component 1760. Central-side connectors 1752 are anchored in steam chamber block (also referred to as "central-side plate") 1758, for which proximal 1756 and distal 1757 sides are depicted. Peripheral-side connectors 1753 are anchored in peripheral plate 1755 and protrude from interface-side peripheral edge 1744 of peripheral plate 1755. The interfaces shown in this and the following figures may be usable in both the upstream and downstream apparatuses, although the sterilization step may be optional for the downstream apparatus.

Figure 18:
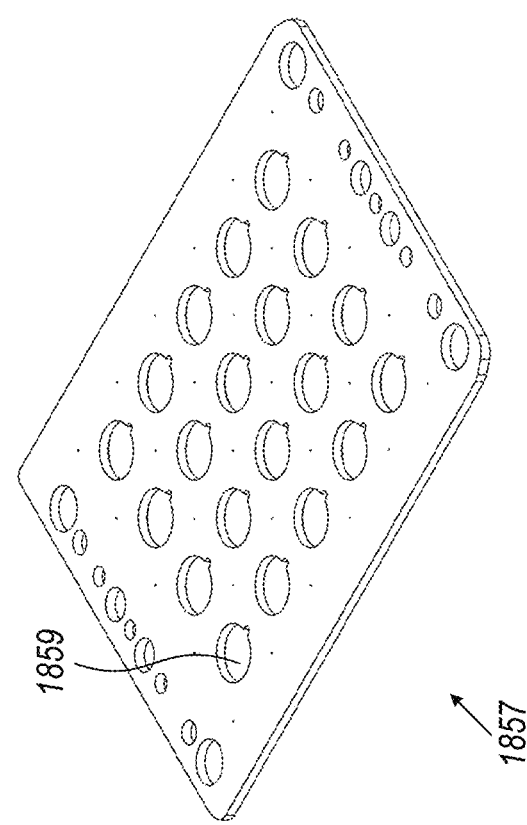
FIG. 18 shows a disassembled, cross-sectional view of proximal and distal plates of a described steam chamber block.
Figure 18:
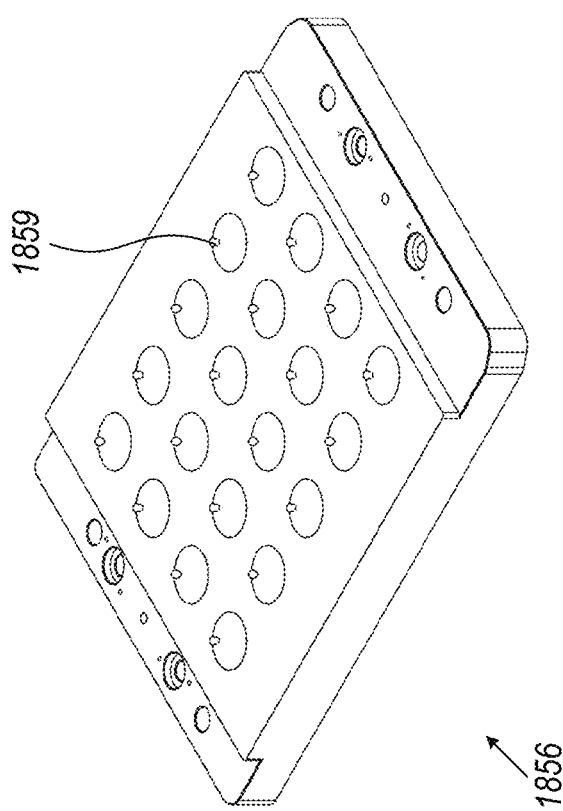

FIG. 18 shows a cross-sectional view, in the plane of connection and transverse to the direction of liquid flow (not depicted), in which steam chamber block (shown assembled in the previous figure) is bisected into proximal 1856 and distal 1857 sides, with distal side 1857 flipped both vertically and horizontally, such that right edges of distal side 1857 (proximal to alignment pin 1751 in the previous figure) appears on left side in this figure, in accordance with principles of the disclosure. Steam routing channels 1859 of steam chamber block are depicted.

Figure 19:
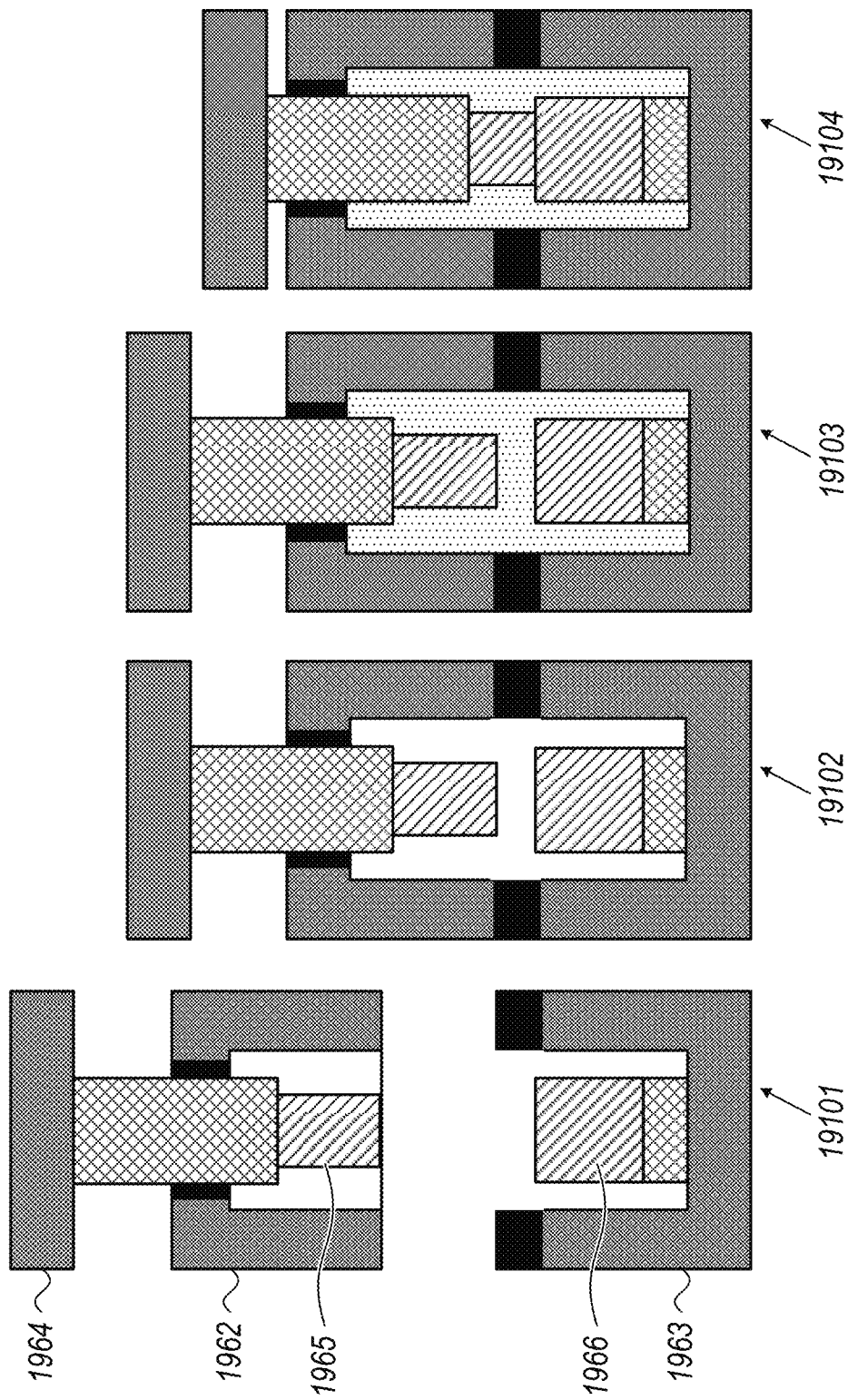
FIG. 19 is a schematic depiction of a described 4-step interface connection and sterilization process.

FIG. 19 is a schematic depiction of a 4-step interface connection and sterilization process, in accordance with principles of the disclosure. Components are depicted schematically. In step 1/disconnected mode 19101, two halves of chamber enclosure, namely center-side 1962 and peripheral-side 1963 chamber enclosure components, are disconnected. In step 2/chamber connected mode 19102, center-side 1962 and peripheral-side 1963 chamber enclosure components are juxtaposed by action of actuator linear 1964, thereby forming airtight chamber seal, while fluid connector plug 1965 and socket 1966 remain detached. In step 3/steam sterilization 19103, steam is pumped into system via steam routing channels (see previous figure), thereby sterilizing chamber. In step 4/fluidic connected mode 19104, plug 1965 and socket 1966 fluid connectors are juxtaposed by further action of actuator 1964 to form fluid connection.

Figure 20:
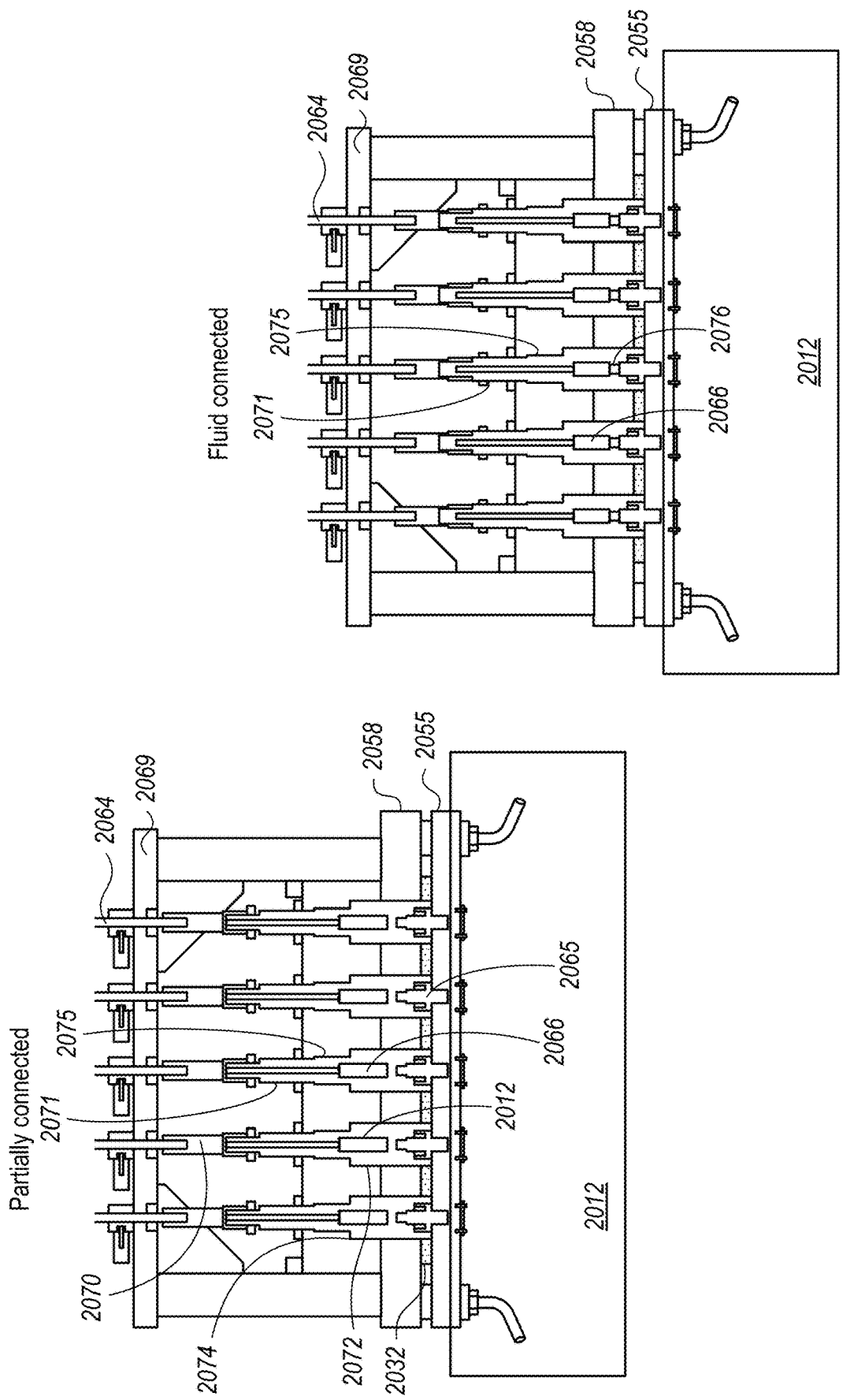
FIG. 20 depicts a side view of a central side component of a described interface and its connection to a peripheral compartment.

FIG. 20 depicts a side view of the central side component of an interface and its connection to a peripheral compartment (which may be also referred to as "slow module"), depicted schematically as box 2012, in accordance with principles of the disclosure. Actuator 2064 traverses central-side plate 2069 via apertures (not depicted) and rigidly connects to coupler 2070, which in turn rigidly connects to piston 2071 and chamber housing 2072. Directions of motion of linear actuator 2064 and (future) fluid/air flow path are represented by 2-headed arrows. Prior to chamber-connected mode, peripheral plate 2055 has been placed and rigidly secured (for example, with bolts [not depicted]) against gasket seal 2032. Peripheral plate 2055 may have been pre-sterilized separately, e.g., in an autoclave.

In chamber-connected mode (left panel; paralleling step 2 of the previous figure), actuator 2064 has engaged coupler 2070 and exerted force to move coupler 2070 to an intermediate downward position, with piston 2071 and chamber housing 2072 moving downward accordingly.

By virtue of this downward motion, lower edge of chamber housing 2072 traverses gasket seal 2032 and presses against peripheral plate 2055, thus forming a closed and airtight steam chamber 2074. Steam chamber 2074 is maintained in closed position via piston seal 2075. Fluid connector plug 2065 and socket 2066 remain detached from one another.

In the next step (not depicted; paralleling step 3 of the previous figure), steam chamber 2074 is steam-sterilized through chambers formed by the peripheral plate 2055 and (central-side) steam chamber block 2058. Steam is routed through steam chamber block 2058 from several inlets (not depicted).

In fluid-connected mode (right panel; paralleling step 4 of the previous figure), actuator has fully engaged downward to move fluid connector plug 2065 downward, thus mating with socket 2066 to form fluid connection 2076. Fluid connections 2076 may be simultaneously or independently actuated.

Figure 21:
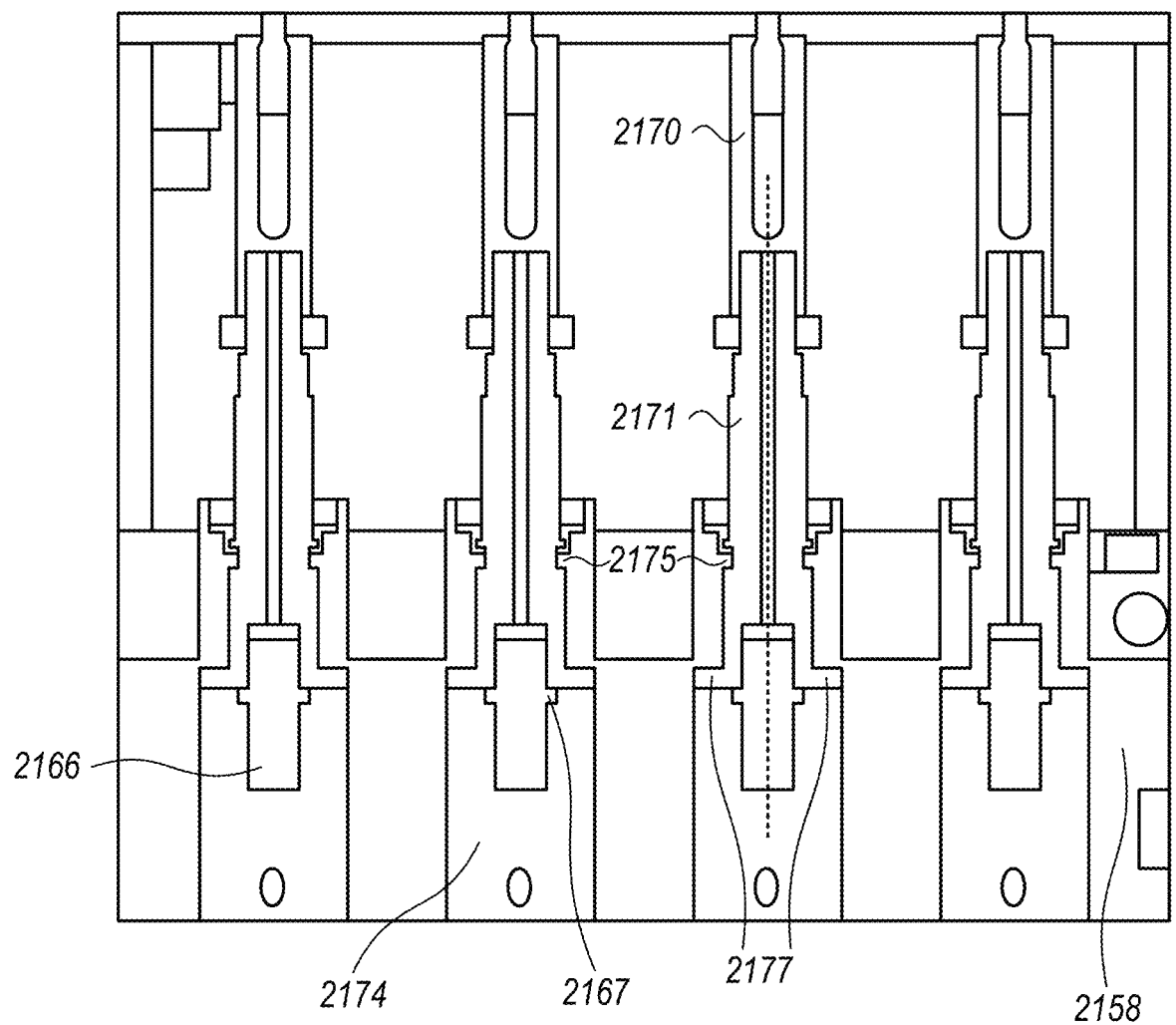
FIG. 21 depicts a magnified view of the coupling apparatus of the central side component shown in the previous figures.

FIG. 21 depicts a magnified view of the coupling apparatus of the central side component shown in the previous figure, in fully retracted (disconnected) position, showing couplers 2170, piston 2171, steam chamber block 2158, socket 2166, including protruding portion 2167, and piston seal 2175, which seals the interface between upper piston and steam chamber block. Dotted line depicts fluid flow path. Piston distal edge 2177 abuts both steam chamber 2174 and socket protruding portion 2167 to form a steam-tight seal.

Figure 22:
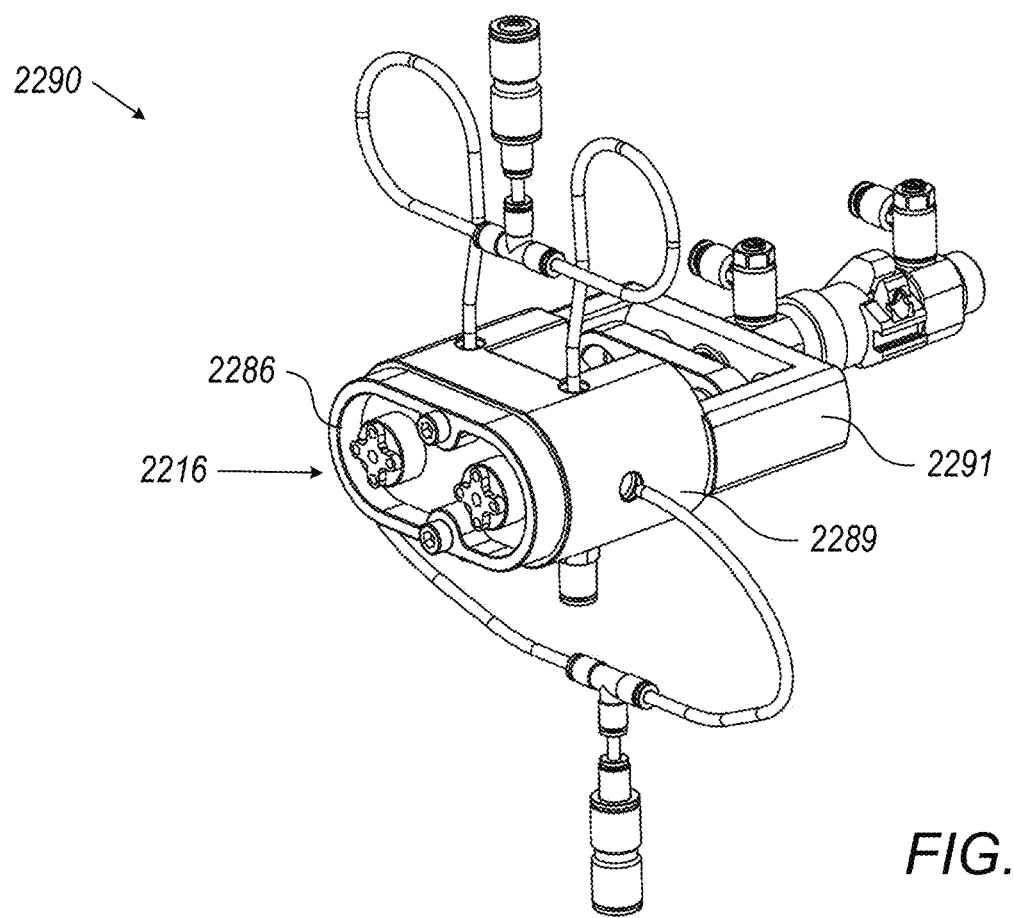
FIG. 22 depicts a perspective view of a described connecting apparatus, including a central side component of an interface and components disposed proximally thereto.

FIG. 22 depicts a perspective, isolated view of the central side component 2290 of interface 2216 for additional peripheral compartment (also referred to as "fast module interface"), in accordance with principles of the disclosure. Depicted are fast module gasket seal 2286, chamber housing block 2289, and actuator mount 2291. The mechanism of attachment of fast module and its individual connectors may be similar to that of slow module.

Figure 23:
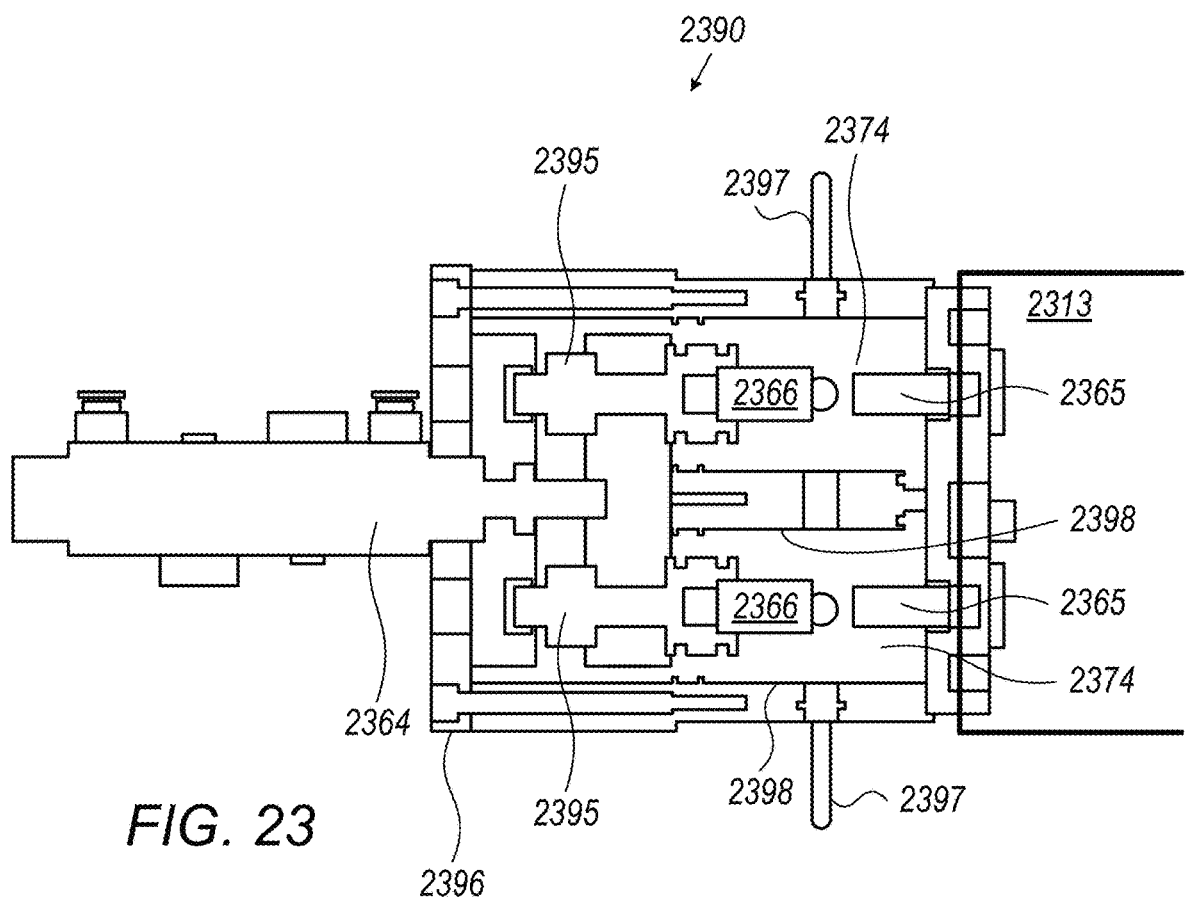
FIG. 23 depicts a top, cross-sectional view of a central side component of a described interface.

FIG. 23 depicts a top, cross-sectional view, sectioned longitudinally through the steam chambers 2374, of central side component 2390 of interface for additional peripheral compartment (also referred to as "fast module interface"), in accordance with principles of the disclosure. Steam chambers 2374 are depicted in chamber-connected, but fluid-disconnected, position/mode, in which fluid connector plugs 2365 and sockets 2366 are separated. Fast module 2313 is depicted schematically as a box. Proximal ends 2395 of fluid connectors are depicted. Proximal end 2396 of central side component 2390 may be rigidly connected to remainder of central compartment, for example by attachment to a plate (not depicted) mounted on a rigid frame. Tubing 2397 is described for the next figure (see description of peripheral inlet lines). When fast module 2313 is connected to central side component 2390, fluid connector plugs 2365 insert into lumen of steam chambers 2374. Subsequent force provided by linear actuator 2364 moves fluid connector sockets 2366 rightward, causing them to mate with plugs 2365 as depicted in FIG. 19-20. Cooling channels (not depicted) approximately one millimeter in diameter surround outer edges 2398 of steam chambers 2374, acting as a water jacket to enable rapid cooling after steam sterilization.

Figure 24:
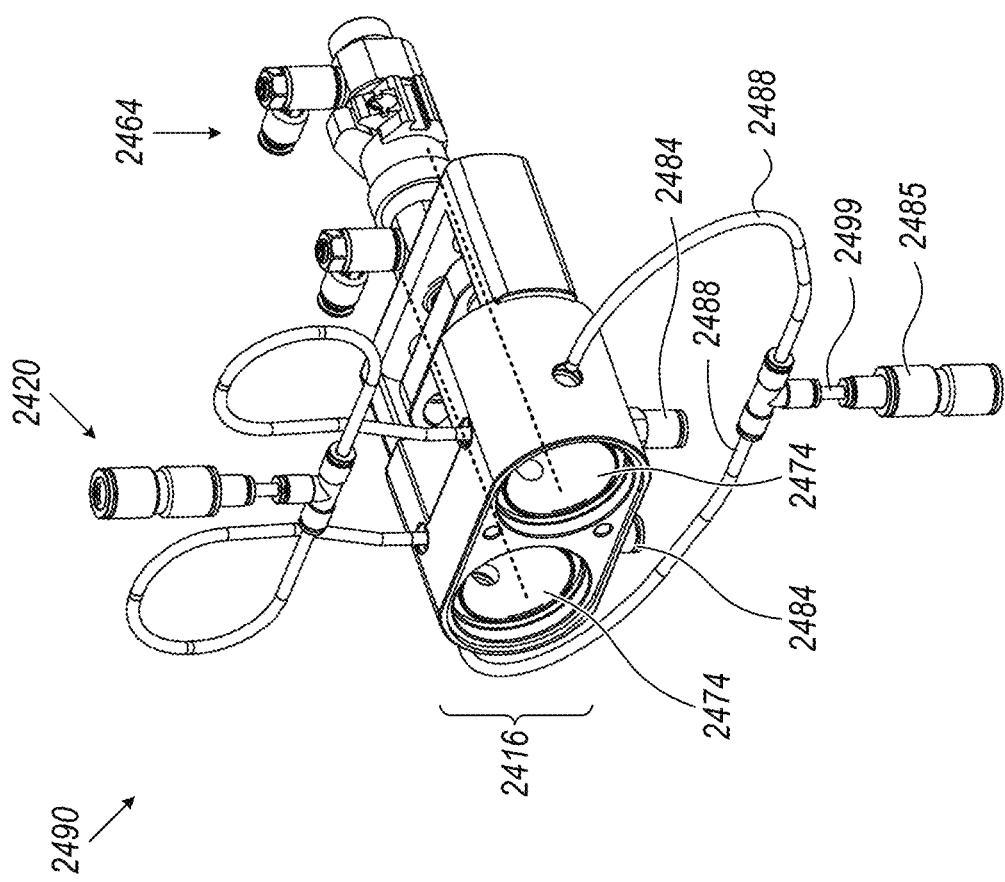
FIG. 24 depicts a perspective view of a central side component of a described interface.

FIG. 24 depicts a perspective, isolated view of the central side component 2490 of fast module interface, attached to linear actuator 2464, in accordance with principles of the disclosure. Cutaway view, with fast module gasket seal removed, enables visualization of steamable connection chambers (also referred to as "steam chambers") 2474.

Cooling inlet/outlet tubes 2484 enable circulation of water from a pump (not depicted) through cooling channels (see description of previous figure). Steam inlet connector 2485 is also depicted.

Steam for sterilization first passes through a single inlet line 2499, which splits into two peripheral inlet lines 2488, one for each steam chamber 2474. Steam exits via chamber steam outlet tubing 2420.

Fluid flow through the interface 2416 is depicted by dotted lines. Fluid paths within central side component 2490 are not visible in this view.

Figure 25:
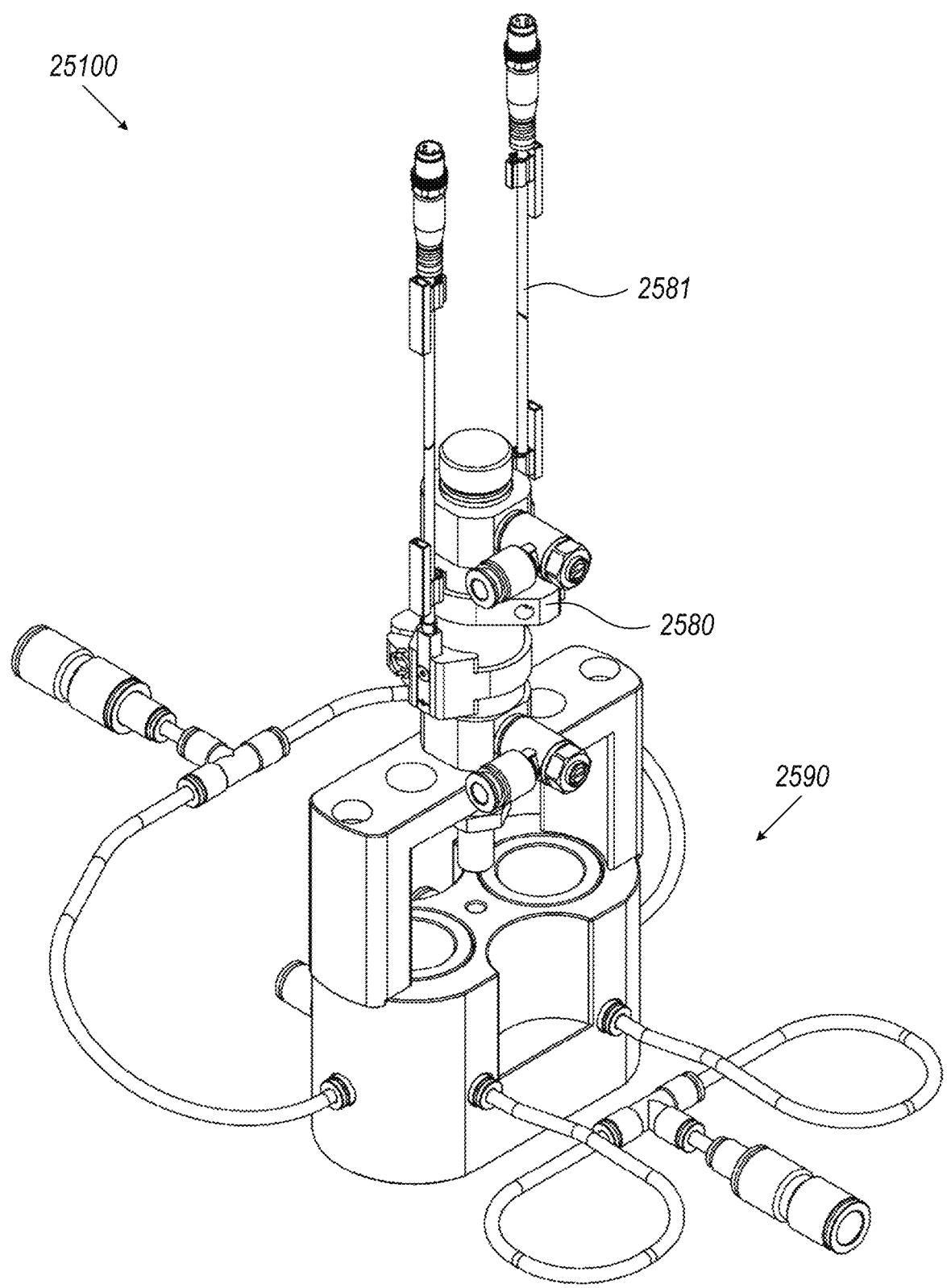
FIG. 25 depicts a perspective view of a described connecting apparatus, including a central-side interface component and components disposed proximally thereto.

FIG. 25 depicts a perspective view of "fast" connecting apparatus 25100, including the central-side component 2590 of fast module interface and components disposed proximally (internally) thereto, including actuators 2580 and actuator sensor cables 2581, in accordance with principles of the disclosure.

Figure 26:
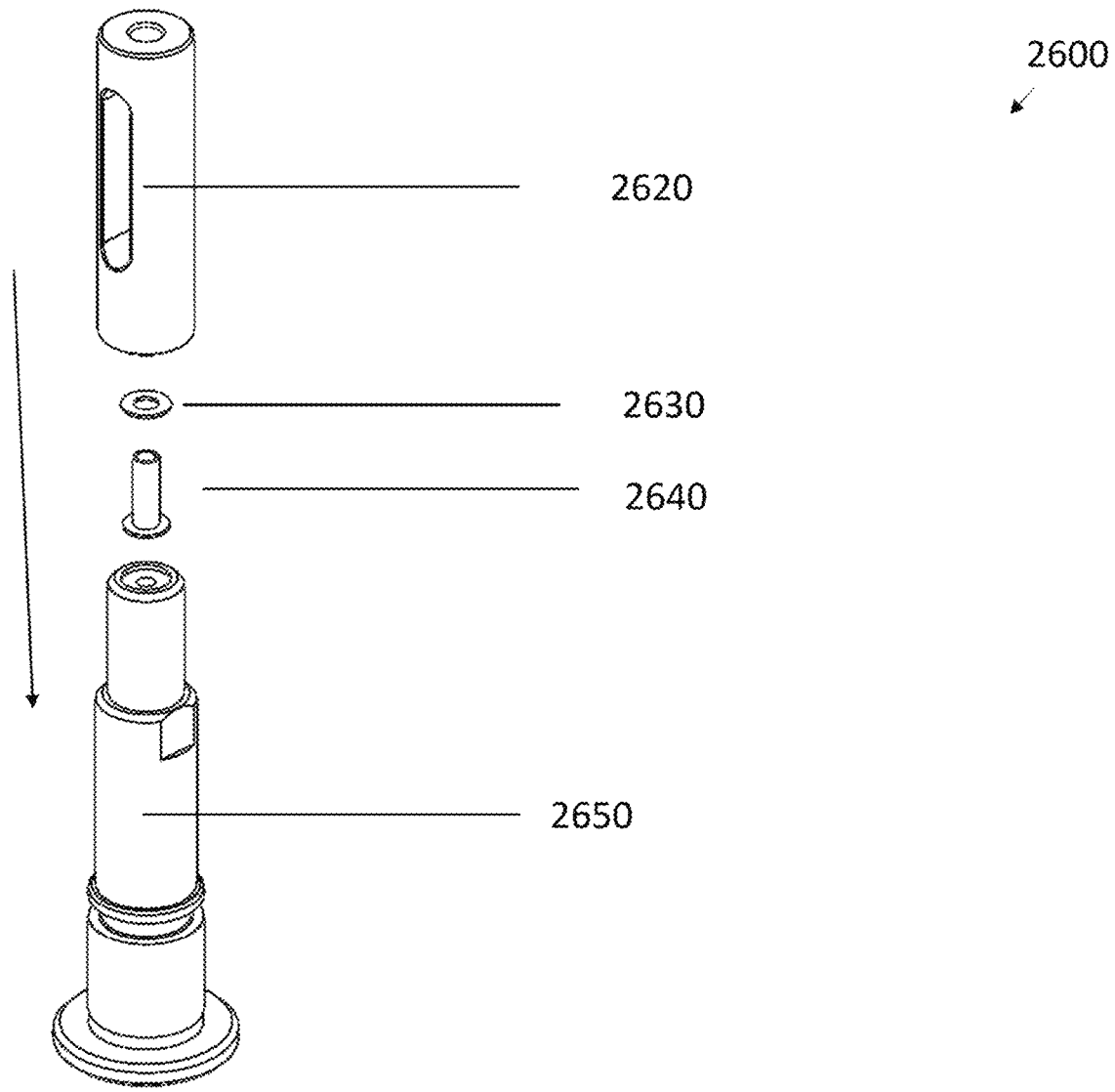
FIG. 26 is an exploded view of a piston flanged tube assembly.

FIG. 26 is an exploded view of a flanged tube 2600. Direction of assembly is shown by arrow. Depicted are retaining piece 2620, locating washer 2630, flanged tube 2640, and connection body 2650.

Figure 27:
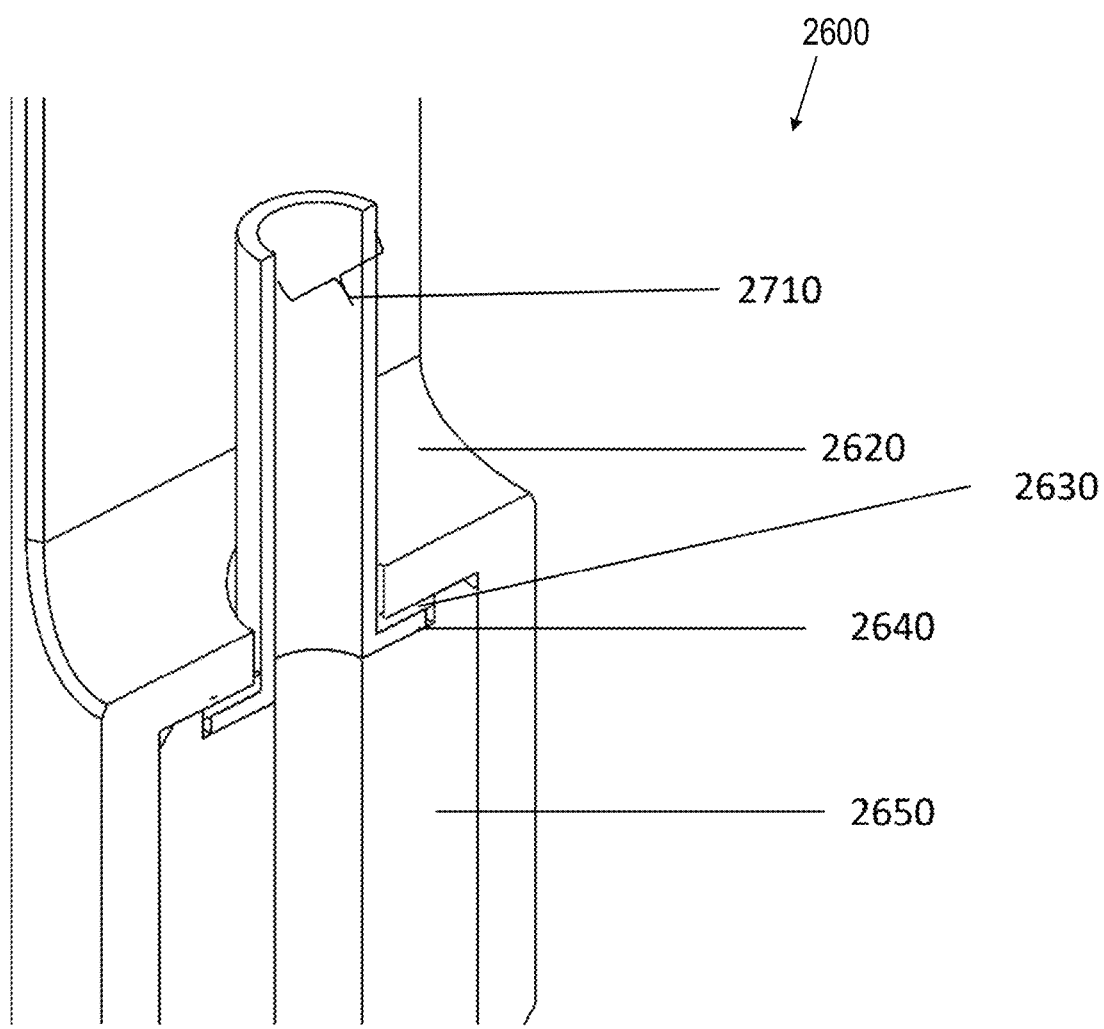
FIG. 27 is a magnified cross section of a flanged tube assembly.

FIG. 27 is a magnified cross section of a flanged tube assembly 2600, showing continual internal bore, as well as retaining piece 2620, locating washer 2630, flanged tube 2640, and connection body 2650.

Figure 28:
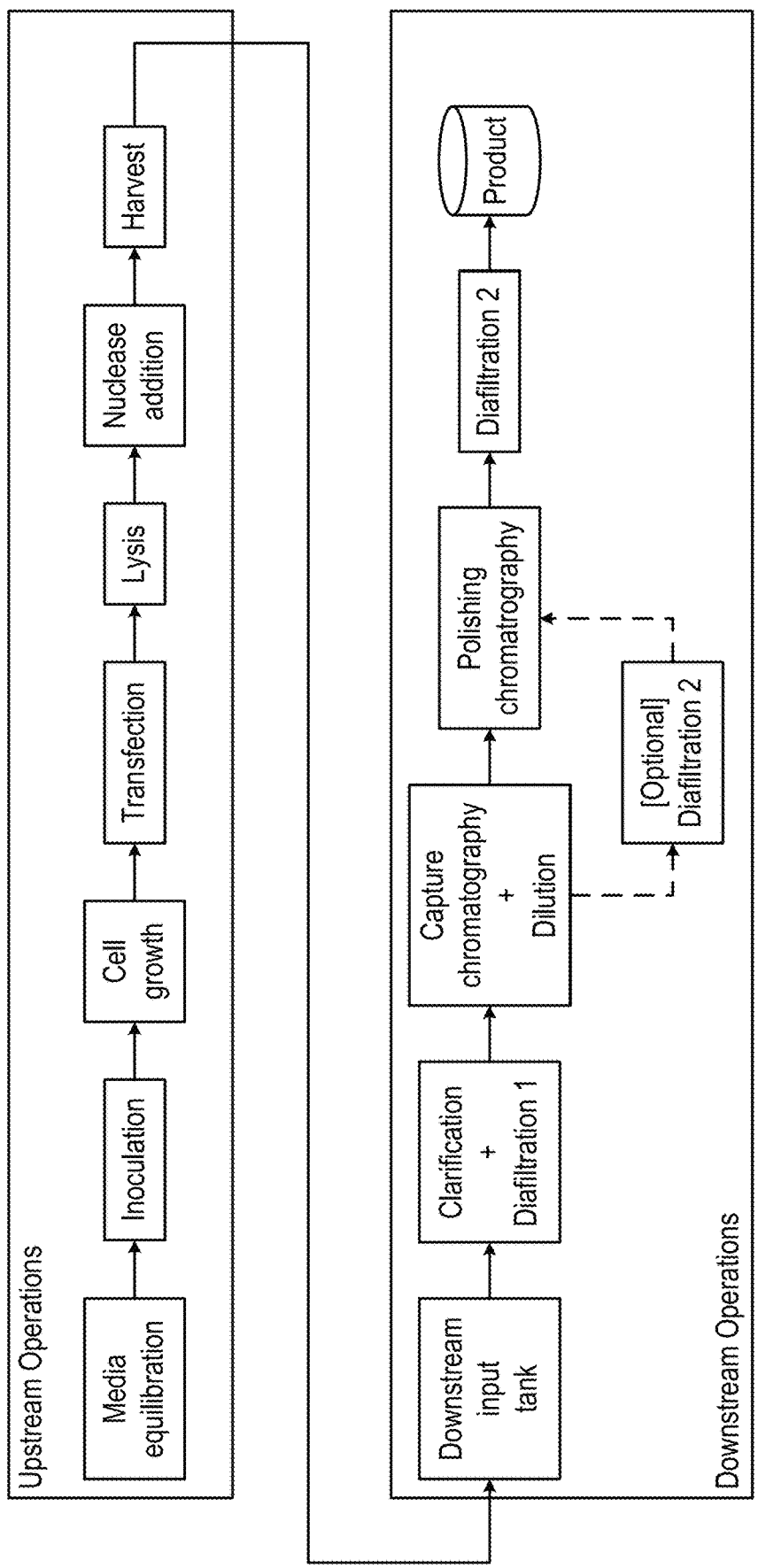
FIG. 28 is a flow chart depicting a consolidated method for growing, harvesting, and purifying virus particles.

FIG. 28 is a flow chart depicting an exemplary consolidated method for growing, harvesting, and purifying virus particles, in accordance with principles of the disclosure.

In step 1, Media Equilibration, the bioreactor is clean, sterile, and ready to run with the "slow addition" module attached. Media is added, and conditions in the reactor (e.g., temperature, pH, dissolved oxygen [$DO_2$]) are equilibrated and controlled.

In step 2, Inoculation, cells are added to the bioreactor manually using the "fast addition" module.

In step 3, Cell Growth, bioreactor conditions continue to be maintained to promote cell growth. Cells expand to desired density. This step typically continues for 3-10 days.

In step 4, Transfection, plasmid and transfection reagent are added via the "fast addition" module to initiate viral transfection. This step typically continues for 1-3 days.

In step 5, Lysis, lysis buffer is added to initiate breakdown of cells to release viral particles.

In step 6, Nuclease Addition, nuclease is added to digest host cell chromatin.

In step 7, Harvest, product is transferred from bioreactor to hold tank for downstream operations.

In step 8. Clarification+Diafiltration 1, initial lysate filtration is performed, and buffer is exchanged for concentrating buffer compatible with the capture step.

In step 9, Capture Chromatography+Dilution, product is captured via chromatography, and the buffer is subsequently diluted to lower the salt concentration.

In optional step 9B, Supplemental Diafiltration, the diafiltration step is repeated.

In step 10, Polishing Chromatography, empty and full capsids are separated.

In step 11, Final Diafiltration, buffer is exchanged into the final formulation buffer. Product may be concentrated, if required.

One of ordinary skill in the art will appreciate that the steps shown and described herein may be performed in other than the recited order and that one or more steps illustrated may be optional.

Thus, methods, systems, and apparatuses products may improve and optimize biotechnological processes, such as cell culture and downstream purification steps. Persons skilled in the art will appreciate that the present invention can be practiced by other than the described embodiments, which are presented for purposes of illustration rather than of limitation.

What is claimed is:

1. A system for processing a liquid sample, the system comprising a first component and a second component, the second component being distinct from the first component and reversibly connected to the first component, wherein:
the first component comprises:
  an interface side, the interface side comprising at least 4 orifices, wherein the at least 4 orifices comprise a first orifice, a second orifice, a third orifice, and a fourth orifice;
  a first pressure actuator;
  at least 2 sample containers, wherein the at least 2 sample containers comprise a first sample container and a second sample container;
  a first gas conduit, the first gas conduit connecting the first sample container to the first pressure actuator and configured to transmit pressure from the first pressure actuator to the first sample container and impel a sample out of the first sample container;
  at least 4 connectors, wherein the at least 4 connectors comprise a first connector, a second connector, a third connector, and a fourth connector;
  at least 2 sample conduits, wherein the at least 2 sample conduits comprise a first sample conduit and a second sample conduit;
  and
  a reagent conduit;
  wherein:
    the first sample conduit is connected to the first sample container and the first connector,
    the second sample conduit is connected to the second sample container and the second connector;
    the reagent conduit is connected to the third and fourth connectors; and
    the first, second, third, and fourth connectors are disposed in the first, second, third, and fourth orifices, respectively;
the second component comprises:
  a connector manifold, the connector manifold comprising at least 4 connectors, wherein the at least 4 connectors comprise a fifth connector, a sixth connector, a seventh connector, and an eighth connector;
  a fractionation moiety, the fractionation moiety being reversibly connected to the fifth, sixth, and seventh connectors and configured to perform a biochemical fractionation procedure; and
  a reagent container reversibly connected to the eighth connector;
the first connector is reversibly connected to the fifth connector;
the second connector is reversibly connected to the sixth connector;
the third connector is reversibly connected to the seventh connector; and
the fourth connector is reversibly connected to the eighth connector.

2. The system of claim 1, wherein the system further comprises a first mass sensor and a second mass sensor, the first and second mass sensors being configured to weigh the first and second sample containers, respectively.

3. The system of claim 1, wherein the system is configured to:
route the liquid sample from the first sample container to the fractionation moiety, and from the fractionation moiety to the second sample container; and
route a reagent from the reagent container to the fractionation moiety.

4. The system of claim 1, wherein:
the first component further comprises:
  a third sample container;
  optionally a second pressure actuator;
  a second gas conduit, the second gas conduit connecting the second sample container to the first pressure actuator or the second pressure actuator and configured to transmit pressure from the first or second pressure actuator to the second sample container and impel a sample out of the second sample container;
  at least 2 additional sample conduits, wherein the at least 2 additional sample conduits comprise a third sample conduit and a fourth sample conduit; and
  at least 2 additional connectors, wherein the at least 2 additional connectors comprise a ninth connector and a tenth connector;

the second component further comprises:
- at least 2 additional connectors, wherein the at least 2 additional connectors comprise an eleventh connector and a twelfth connector, both disposed in the connector manifold; and
- a second fractionation moiety reversibly connected to the eleventh and twelfth connectors and configured to perform a biochemical fractionation procedure;

the third sample conduit is connected to the ninth connector;

the fourth sample conduit is connected to the tenth connector;

the ninth connector is connected to the eleventh connector; and the tenth connector is connected to the twelfth connector.

5. The system of claim 1, wherein the first, second, third, and fourth connectors comprise an internal flanged tube component.

* * * * *